US010258046B2

(12) United States Patent
Grossman et al.

(10) Patent No.: US 10,258,046 B2
(45) Date of Patent: *Apr. 16, 2019

(54) ANTIMICROBIAL COATINGS COMPRISING QUATERNARY SILANES

(71) Applicant: ALLIED BIOSCIENCE, INC., Dallas, TX (US)

(72) Inventors: Craig Grossman, Point Roberts, WA (US); Gavri Grossman, Point Roberts, WA (US); Daniel Moros, New York, NY (US); Jie Fang, Delta (CA)

(73) Assignee: ALLIED BIOSCIENCE, INC., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/969,576

(22) Filed: May 2, 2018

(65) Prior Publication Data

US 2018/0242585 A1    Aug. 30, 2018

Related U.S. Application Data

(63) Continuation-in-part of application No. 15/432,413, filed on Feb. 14, 2017, which is a continuation of application No. 15/041,974, filed on Feb. 11, 2016, now Pat. No. 9,918,475, which is a continuation-in-part of application No. 14/932,840, filed on Nov. 4, 2015, now Pat. No. 9,856,360.

(60) Provisional application No. 62/114,998, filed on Feb. 11, 2015, provisional application No. 62/075,020, filed on Nov. 4, 2014.

(51) Int. Cl.
| | |
|---|---|
| *C09D 183/08* | (2006.01) |
| *A01N 55/00* | (2006.01) |
| *A01N 33/08* | (2006.01) |
| *A61L 2/00* | (2006.01) |
| *B05D 1/02* | (2006.01) |
| *B05D 7/14* | (2006.01) |
| *B05D 7/00* | (2006.01) |
| *C09D 5/14* | (2006.01) |
| *C09D 179/02* | (2006.01) |
| *C23C 26/00* | (2006.01) |
| *A01N 59/16* | (2006.01) |
| *A01N 25/02* | (2006.01) |
| *C09D 7/61* | (2018.01) |
| *B05B 5/025* | (2006.01) |
| *A61L 2/08* | (2006.01) |
| *A61L 2/232* | (2006.01) |
| *C08K 3/22* | (2006.01) |
| *C09D 183/00* | (2006.01) |
| *C08G 77/26* | (2006.01) |

(52) U.S. Cl.
CPC ............ *A01N 55/00* (2013.01); *A01N 25/02* (2013.01); *A01N 33/08* (2013.01); *A01N 59/16* (2013.01); *A61L 2/00* (2013.01); *A61L 2/088* (2013.01); *A61L 2/232* (2013.01); *B05B 5/0255* (2013.01); *B05D 1/02* (2013.01); *B05D 7/14* (2013.01); *B05D 7/544* (2013.01); *C09D 5/14* (2013.01); *C09D 7/61* (2018.01); *C09D 179/02* (2013.01); *C09D 183/08* (2013.01); *C23C 26/00* (2013.01); *A01N 2300/00* (2013.01); *C08G 77/26* (2013.01); *C08K 3/22* (2013.01); *C08K 2003/2241* (2013.01); *C09D 183/00* (2013.01)

(58) Field of Classification Search
CPC ................................. C09D 183/08; C09D 5/14
See application file for complete search history.

(56) References Cited

U.S. PATENT DOCUMENTS

| | | | |
|---|---|---|---|
| 3,068,199 A | 12/1962 | Sellers | |
| 3,133,108 A | 5/1964 | Finestone | |
| 4,005,025 A | 1/1977 | Kinstedt | |
| 4,048,206 A | 9/1977 | Voronkov et al. | |
| 4,740,538 A | 4/1988 | Sekutowski | |
| 4,865,844 A * | 9/1989 | Blank | A61K 31/695 424/409 |
| 5,359,104 A * | 10/1994 | Higgs | C07F 7/1804 556/406 |
| 5,411,585 A | 5/1995 | Avery et al. | |
| 5,879,436 A | 3/1999 | Kramer | |
| 5,945,555 A | 8/1999 | Yoshitake | |
| 5,954,869 A | 9/1999 | Elfersy | |
| 7,704,561 B2 | 4/2010 | Mehta et al. | |
| 8,491,922 B2 | 7/2013 | Eddy | |
| 8,951,341 B2 | 2/2015 | Jaffrennou | |
| 8,968,771 B2 | 3/2015 | Richardson et al. | |

(Continued)

FOREIGN PATENT DOCUMENTS

| | | |
|---|---|---|
| CN | 103305029 | 3/2013 |
| CN | 103351916 | 10/2013 |

(Continued)

OTHER PUBLICATIONS

Office Action dated May 29, 2018 in Canadian Application No. 2965978.

(Continued)

Primary Examiner — Margaret G Moore
(74) Attorney, Agent, or Firm — Snell & Wilmer L.L.P.

(57) ABSTRACT

A method of preparing an antimicrobial coating comprises coating a surface with an aqueous mixture of 3-(trihydroxysilyl)propyl dimethyloctadecyl ammonium chloride, 3-chloropropyltrimethoxysilane, and triethanolamine and then coating the surface with an aqueous titanyl sol-gel solution comprising an aqueous mixture of peroxotitanium acid and peroxo-modified anatase sol overtop of the silane to form the antimicrobial coating. The antimicrobial coating exhibits residual antimicrobial efficacy against *E. coli* and *S. epidermidis* after water rinsing or after abrasion. The use of 3-chloropropyltrimethoxysilane was found to improve storage stability of the quaternary silane composition and the durability of the antimicrobial coating.

20 Claims, 44 Drawing Sheets

(56) References Cited

U.S. PATENT DOCUMENTS

| | | | |
|---|---|---|---|
| 2003/0101898 A1 | 6/2003 | Standke | |
| 2005/0238839 A1 | 10/2005 | Takagi et al. | |
| 2006/0142459 A1 | 6/2006 | Goebel | |
| 2008/0131594 A1 | 6/2008 | Cho | |
| 2009/0030220 A1 | 1/2009 | Uchibori | |
| 2009/0317624 A1 | 12/2009 | Yoshioka | |
| 2010/0029530 A1 | 2/2010 | Whiteley | |
| 2010/0234506 A1 | 9/2010 | Elizalde | |
| 2011/0000539 A1* | 1/2011 | Gronet | H01L 31/02167 136/256 |
| 2012/0015200 A1 | 1/2012 | Ali | |
| 2013/0040078 A1 | 2/2013 | Scharfe et al. | |
| 2013/0167754 A1 | 7/2013 | Wassmer | |
| 2013/0237409 A1* | 9/2013 | Sambandam | B01J 27/24 502/184 |
| 2014/0158018 A1 | 6/2014 | Geoffrion et al. | |
| 2015/0020712 A1 | 1/2015 | Wosylus | |
| 2016/0097595 A1* | 4/2016 | Ritchey | B01D 53/265 165/114 |

FOREIGN PATENT DOCUMENTS

| | | |
|---|---|---|
| JP | 47009016 | 5/1972 |
| JP | 2004204091 | 1/1997 |
| JP | 2000-351940 | 12/2000 |
| JP | 2003181299 | 7/2003 |
| JP | 2004091697 | 3/2004 |
| JP | 2004204091 | 7/2004 |
| JP | 2004224861 | 8/2004 |
| JP | 2004231887 | 8/2004 |
| JP | 2004337740 | 12/2004 |
| JP | 2005131072 | 5/2005 |
| JP | 2005138059 | 6/2005 |
| JP | 2005199155 | 7/2005 |
| JP | 2005246639 | 9/2005 |
| JP | 2006136758 | 6/2006 |
| JP | 2006136782 | 6/2006 |
| JP | 2006-526686 | 11/2006 |
| JP | 2006337740 | 12/2006 |
| JP | 2008073588 | 4/2008 |
| JP | 2008188583 | 8/2008 |
| JP | 2008276145 | 11/2008 |
| JP | 2010-111793 | 5/2010 |
| JP | 201126941 | 6/2011 |
| JP | 06287068 | 5/2012 |
| JP | 2013032474 | 2/2013 |
| JP | 20108502975 | 2/2018 |
| KR | 1020060045901 A | 5/2006 |
| RU | 2450516 | 10/1994 |
| RU | 2470053 | 12/2012 |
| SU | 346315 | 7/1972 |
| SU | 1130570 | 12/1984 |
| SU | 1567314 | 5/1990 |
| WO | 2007012026 | 1/2007 |
| WO | 2007097284 | 8/2007 |
| WO | 2011059101 | 5/2011 |
| WO | 2011099510 | 8/2011 |
| WO | 2012037615 | 3/2012 |
| WO | 2012142621 | 10/2012 |
| WO | 2013082096 | 6/2013 |
| WO | 2013156327 | 10/2013 |
| WO | 2014089560 | 6/2014 |
| WO | 2016073634 | 5/2016 |

OTHER PUBLICATIONS

Office Action dated May 29, 2018 in Australian Application No. 2016219202.
Final Office Action dated Jul. 20, 2018 in U.S. Appl. No. 15/432,443.
Notice of Allowance dated Aug. 22, 2018 in Japanese Application No. 2017-536331.
Exam Report dated Aug. 30, 2018 in Euporean Application 15857660.3.
Final Office Action dated Aug. 31, 2018 in U.S. Appl. No. 15/432,413.
Final Office Action dated Aug. 31, 2018 in U.S. Appl. No. 15/432,428.
WIPO; International Search Report and Written Opinion dated Feb. 23, 2016 in Application No. PCT/US2015/059080.
WIPO; International Search Report and Written Opinion dated May 27, 2016 in Application No. PCT/US2016/017599.
USPTO; Restriction Requirement dated Dec. 22, 2106 in U.S. Appl. No. 14/932,840.
Moros, et al., U.S. Appl. No. 15/432,567, filed Feb. 14, 2017 and entitled "Synergistic Combinations of Choline and Reactive Silanes in Antimicrobial Coatings".
Moros, et al., U.S. Appl. No. 15/432,443, filed Feb. 14, 2017 and entitled "Antimicrobial Coatings Formed by Reaction of Silanes With Triethanolamine to Form Polymeric Siloxanes".
Moros, et al., U.S. Appl. No. 15/432,428, filed Feb. 14, 2017 and entitled "Methods of Preparing Reactive Mixtures of Silanes and Triethanolamine and Polymers Therefrom".
USPTO, Office Action dated Mar. 15, 2017 in U.S. Appl. No. 14/932,840.
USPTO, Office Action dated Apr. 3, 2017 in U.S. Appl. No. 15/432,567.
USPTO, Restriction Requirement dated May 25, 2017 in U.S. Appl. No. 15/041,974.
USPTO, Final Office Action dated Jun. 30, 30, 2017 in U.S. Appl. No. 15/432,567.
USPTO, Final Office Action dated Aug. 9, 2017 in U.S. Appl. No. 14/932,840.
Examination Report dated Sep. 28, 2017 in Australian Application No. 2015343153.
USPTO, Office Action dated Apr. 5, 2018 in U.S. Appl. No. 15/432,428.
USPTO, Office Action dated Apr. 2, 2018 in U.S. Appl. No. 15/432,443.
USPTO, Notice of Allowance dated Sep. 8, 2017 in U.S. Appl. No. 15/432,567.
USPTO, Non-Final Office Action dated Nov. 17, 2017 in U.S. Appl. No. 15/041,971.
WIPO, International Preliminary Report on Patentability dated May 9, 2017 in Application No. PCT/US2015/059080.
WIPO, International Preliminary Report on Patentability dated Aug. 15, 2017 in Application No. PCT/US2016/017599.
USPTO, Notice of Allowance dated Jan. 3, 2018 in U.S. Appl. No. 15/041,974.
USPTO, Notice of Allowance dated Oct. 24, 2017 in U.S. Appl. No. 14/932,840.
Moros, et al., U.S. Appl. No. 15/718,997, filed Sep. 29, 2017 and entitled "Antimicrobial Coatings Capable of Reducing the Number of Murine Norovirus Inoculated Thereon".
Moros, et al., U.S. Appl. No. 15/720,835, filed Sep. 29, 2017 and entitled "Methods of Coating a Surface With an Antimicrobial Coating Capable of Reducing the Number of Murine Norovirus Inoculated Thereon".
Office Action dated Apr. 12, 2018 in Canadian Application No. 2,972,923.
Office Action dated Apr. 25, 2018 in Japanese Patent Application No. 2017-543303.
Office Action dated Jun. 15, 2018 in Russian Application No. 2017124203.
Grossman, et al., U.S. Appl. No. 15/969,576, filed May 2, 2018, entitled "Antimicrobial Coatings Comprising Quaternary Silanes".
Examination Report No. 2 dated Mar. 1, 2018 in Australian Application No. 2015343153.
Notice of Acceptance for Patent Application dated May 15, 2018 in Australian Application No. 2015343153.
Notice of Preliminary Rejection dated May 4, 2018 in Korean Application No. 10-2017-7014833.
Notice of Allowance dated Aug. 22, 2018 in Canadian Application No. 2965978.
Notice of Allowance dated Oct. 11, 2018 in U.S. Appl. No. 15/432,443.
Advisory Action dated Nov. 8, 2018 in U.S. Appl. No. 15/432,428.
Advisory Action dated Nov. 14, 2018 in U.S. Appl. No. 15/432,413.

(56) References Cited

OTHER PUBLICATIONS

Office Actin dated Oct. 10, 2018 in Japanese Application No. 2017-543303.
Final Office Action dated Oct. 18, 2018 in Korean Application No. 10-2017-7014833.
Notice of Allowance dated Nov. 28, 2018 in Korean Application No. 10-2017-7014833.
Notice of Allowance dated Nov. 29, 2018 in U.S. Appl. No. 15/432,413.
Notice of Allowance dated Dec. 26, 2018 in U.S. Appl. No. 15/432,428.

* cited by examiner

| Organism | Culture method | Incubation conditions | Further analysis |
|---|---|---|---|
| Total bacteria ) | Spread plating on R2A medium (BD Diagnostics, Sparks, MD. | 24 °C for 5 days | |
| *C. difficile* | Incubation for 7 days in 0.1% sodium taurocholate and cycloserine-cefoxin fructose broth | Anaerobic conditions at 37 °C for up to 5 days | A 2-mL aliquot was mixed with equal amounts of absolute ethanol. Bacteria were concentrated by centrifugation and pellets were used to inoculate cycloserine-cefoxtin fructose agar. |
| MRSA | Trypticase soy agar amended with 5% sheep's blood, 10 mg/L colistin, and 25 mg/ naladixic acid using spread plate method | 35 °C for 24-48 hours | B-hemolytic colonies were isolated and sub-cultured on trypticase case soy agar with no amendments and incubated at 35 °C for 24-48 hours. |
| CRE | Modified Hodge Test; Muller Hinton agar | 35 °C for 24 hours | |
| VRE | Bile esculin azide agar | 37 °C in CO$_2$ incubator for 24-48 hours | Gram stain, catalase test |

*from an original volume of 4 ml of sponge stick eluate. A 0.1 mL volume of this eluate was used for each assay.

FIG. 5

Average (arithmetic mean) total bacterial numbers (colony forming units) on 100 $cm^2$ from fomites and percent reduction after treatment

| | Baseline* | Weeks after treatment | | | | |
| --- | --- | --- | --- | --- | --- | --- |
| | | 1 | 2 | 4 | 8 | 15 |
| Number of Samples | 95 | 81 | 64 | 64 | 64 | 45 |
| Avg number of bacteria | 233,064 | 98 | 80 | 43 | 2,247 | 3,320 |
| Range | 10-7,000,000 | 10-2,500 | 10-840 | 10-2,500 | 10-44,000 | 10-57,000 |
| % reduction | NA | 99.96 | 99.97 | 99.98 | 99.04 | 98.58 |

NA = not applicable, * = before treatment

FIG. 6

Percent colony forming units of total bacteria per 100 cm$^2$ exceeding value indicated

| CFU | Baseline* | Weeks after treatment | | | | |
|---|---|---|---|---|---|---|
| | | 1 | 2 | 4 | 8 | 15 |
| >100 | 71.5 | 11.1 | 17.2 | 12.8 | 51.2 | 33.3 |
| >1,000 | 51.5 | 2.4 | 1.5 | 0 | 17.1 | 24.4 |
| >10,000 | 25.2 | 0 | 0 | 0 | 4.6 | 11.1 |

*= before treatment

FIG. 7

Isolation of antibiotic resistant bacteria (percent of positive sites)

| | Baseline* | Weeks after treatment | | | | |
|---|---|---|---|---|---|---|
| | | 1 | 2 | 4 | 8 | 15 |
| Number of samples | 95 | 81 | 64 | 64 | 64 | 45 |
| VRE | 14 | 0 | 0 | 0 | 1 | 0 |
| MRSA | 7 | 0 | 0 | 0 | 0 | 0 |
| CRE | 3 | 0 | 0 | 0 | 0 | 0 |
| *C. difficile* | 0 | 0 | 0 | 0 | 0 | 0 |
| Overall Percentage | 25 | 0 | 0 | 0 | 1.5 | 0 |

*before treatment

FIG. 8

TABLE 9

| E. coli testing on Formica Chips | | | | | |
|---|---|---|---|---|---|
| | 0 Hour | 2 Hour | Log Reduction 2 Hours | 6 Hour | Log Reduction 6 Hours |
| REVERSED ORDER OF COATING APPLICATION | 1,000,000 | 41,000 | 1.39 | 140 | 3.85 |
| Control | 1,000,000 | 800,000 | 0.10 | 37,000 | 1.43 |

FIG. 9

TABLE 10

| MS-2 testing on Formica Chips | | | |
|---|---|---|---|
| | 0 Hour | 2 Hour | Log Reduction 2 Hours |
| REVERSED ORDER OF COATING APPLICATION | 1,000,000 | 16,000 | 3.12 |
| Control | 21,000,000 | 110,000 | 2.28 |

FIG. 10

TABLE 11

| MRSA testing on Formica Chips | | | | | | | |
|---|---|---|---|---|---|---|---|
| | 0 Hour | 2 Hour | Log Reduction 2 Hours | 6 Hour | Log Reduction 6 Hours | 24 Hour | Log Reduction 24 Hours |
| REVERSED ORDER OF COATING APPLICATION | 3,700,000 | 51,000 | 1.86 | 18,000 | 2.31 | 1,200 | 3.49 |
| Control | 3,700,000 | 2,300,000 | 0.21 | 58,000 | 1.80 | 5,800 | 2.80 |

FIG. 11

TABLE 12

| E. coli testing on Formica Chips | | | | | |
|---|---|---|---|---|---|
| | 0 Hour | 2 Hour | Log Reduction 2 Hours | 6 Hour | Log Reduction 6 Hours |
| SIMULTANEOUS APPLICATION | 1,000,000 | 42,000 | 1.38 | 110 | 3.96 |
| Control | 1,000,000 | 800,000 | 0.10 | 37,000 | 1.43 |

FIG. 12

TABLE 13

| MS-2 testing on Formica Chips | | | |
|---|---|---|---|
|  | 0 Hour | 2 Hour | Log Reduction 2 Hours |
| SIMULTANEOUS APPLICATION | 1,000,000 | 42,000 | 2.70 |
| Control | 21,000,000 | 110,000 | 2.28 |

FIG. 13

TABLE 14

| MRSA testing on Formica Chips | | | | | | | |
|---|---|---|---|---|---|---|---|
|  | 0 Hour | 2 Hour | Log Reduction 2 Hours | 6 Hour | Log Reduction 6 Hours | 24 Hour | Log Reduction 24 Hours |
| SIMULTANEOUS APPLICATION | 3,700,000 | 130,000 | 1.45 | 7,000 | 2.72 | 1,400 | 3.42 |
| Control | 3,700,000 | 2,300,000 | 0.21 | 58,000 | 1.80 | 5,800 | 2.80 |

FIG. 14

TABLE 15

| Test Organism | Contact Time | Sample ID | Bacterial Counts (CFU/Carrier) | Mean Bacterial Count (CFU/Carrier) | Log$_{10}$ Reduction | Percent Reduction |
|---|---|---|---|---|---|---|
| E. coli 25922 | Time Zero | Control | 9.80E+06 | 9.21E+06 | N.A. | |
| | | | 8.65E+06 | | | |
| | | (3-Aminopropyl) triethoxysilane | 8.20E+06 | 8.05E+06 | | |
| | | | 7.90E+06 | | | |

FIG. 15

TABLE 16

| | Contact Time | Sample ID | Bacterial Counts (CFU/Carrier)[a] | Mean Bacterial Count (CFU/Carrier) | Log$_{10}$ Reduction | Percent Reduction |
|---|---|---|---|---|---|---|
| E. coli 25922 | 1 Hour | Control | 3.35E+06 | 3.61E+06 | N.A. | |
| | | | 3.90E+06 | | | |
| | | (3-Aminopropyl) triethoxysilane | ≤ 5.00E+01 | ≤ 5.00E+01 | ≥ 4.86 | ≥ 99.9986 |
| | | | ≤ 5.00E+01 | | | |

[a] "≤": No bacterial colonies observed, therefore counts at or below limit of detection (based on 0.1 ml plating volume)

FIG. 16

TABLE 17

| | Contact Time | Sample ID | Bacterial Counts (CFU/Carrier)* | Mean Bacterial Count (CFU/Carrier) | Log₁₀ Reduction | Percent Reduction |
|---|---|---|---|---|---|---|
| E. coli 25922 | 4 Hours | Control | 2.80E+05 | 3.91E+05 | N.A. | |
| | | | 5.45E+05 | | | |
| | | (3-Aminopropyl) triethoxysilane | ≤ 5.00E+01 | ≤ 5.00E+01 | ≥ 3.89 | ≥ 99.987 |
| | | | ≤ 5.00E+01 | | | |

* "≤": No bacterial colonies observed, therefore counts at or below limit of detection (based on 0.1 ml plating volume)

FIG. 17

TABLE 18

| Test Organism | Contact Time | Sample ID | Bacterial Counts (CFU/Carrier) | Mean Bacterial Count (CFU/Carrier) | Log₁₀ Reduction | Percent Reduction |
|---|---|---|---|---|---|---|
| E. coli 25922 | Time Zero | Control | 9.80E+06 | 9.21E+06 | N.A. | |
| | | | 8.65E+06 | | | |
| | | (3-Chloropropyl) trimethoxysilane | 1.16E+07 | 1.00E+07 | -0.04 | -8.9% |
| | | | 8.70E+06 | | | |

FIG. 18

TABLE 19

| | Contact Time | Sample ID | Bacterial Counts (CFU/Carrier)* | Mean Bacterial Count (CFU/Carrier) | Log$_{10}$ Reduction | Percent Reduction |
|---|---|---|---|---|---|---|
| E. coli 25922 | 1 Hour | Control | 3.35E+06 | 3.61E+06 | N.A. | |
| | | | 3.90E+06 | | | |
| | | (3-Chloropropyl) trimethoxysilane | 1.10E+03 | 2.35E+02 | 4.19 | 99.994% |
| | | | 5.00E+01 | | | |

*"≤": No bacterial colonies observed, therefore counts at or below limit of detection (based on 0.1 ml plating volume)

FIG. 19

TABLE 20

| | Contact Time | Sample ID | Bacterial Counts (CFU/Carrier)ᵃ | Mean Bacterial Count (CFU/Carrier) | Log₁₀ Reduction | Percent Reduction |
|---|---|---|---|---|---|---|
| E. coli 25922 | 4 Hours | Control | 2.80E+05 | 3.91E+05 | N.A. | |
| | | | 5.45E+05 | | | |
| | | (3-Chloropropyl) trimethoxysilane | ≤ 5.00E+01 | ≤ 5.00E+01 | ≥ 3.89 | ≥ 99.987 |
| | | | ≤ 5.00E+01 | | | |

ᵃ "≤": No bacterial colonies observed, therefore counts at or below limit of detection (based on 0.1 ml plating volume)

FIG. 20

TABLE 21

FIG. 21

| | | Untreated | | ABS-G2015E – No TiO2 | | ABS-G2020E – No TiO2 | | ABS-G2030E – No TiO2 | |
|---|---|---|---|---|---|---|---|---|---|
| | | A | B | A | B | A | B | A | B |
| 0 hour | 1.E+04 | 1.36E+07 | 9.70E+06 | 5.20E+06 | 1.13E+07 | 1.50E+07 | 2.60E+07 | 6.20E+06 | 1.10E+07 |
| | 1.E+05 | 1.60E+07 | 9.00E+06 | 4.00E+06 | 2.00E+06 | 0.00E+00 | 2.00E+03 | 4.00E+06 | 0.00E+00 |
| | 1.E+01 | | | | | 0.00E+00 | 0.00E+00 | 0.00E+00 | 0.00E+00 |
| | 1.E+02 | | | | | 0.00E+00 | 0.00E+00 | 0.00E+00 | 0.00E+00 |
| | 1.E+03 | | | | | 0.00E+00 | 0.00E+00 | 0.00E+00 | 0.00E+00 |
| 1 hour | 1.E+04 | 1.30E+07 | 9.10E+06 | 1.90E+06 | 2.60E+06 | 0.00E+00 | 0.00E+00 | 0.00E+00 | 0.00E+00 |
| | 1.E+05 | | | | | 0.00E+00 | 0.00E+00 | 0.00E+00 | 0.00E+00 |
| | 1.E+01 | | | 1.00E+02 | 3.00E+02 | 0.00E+00 | 1.00E+02 | 0.00E+00 | 0.00E+00 |
| | 1.E+02 | | | | 1.50E+04 | 0.00E+00 | 0.00E+00 | 0.00E+00 | 0.00E+00 |
| 4 hour | 1.E+03 | 3.70E+06 | 3.40E+06 | | | 0.00E+00 | 0.00E+00 | 0.00E+00 | 0.00E+00 |
| | 1.E+04 | | | | | 0.00E+00 | 0.00E+00 | 0.00E+00 | 0.00E+00 |
| | 1.E+05 | | | | | 0.00E+00 | 0.00E+00 | 0.00E+00 | 0.00E+00 |

TABLE 22

Log Reduction

| | ABS-G2015E – No TiO2 | ABS-G2020E – No TiO2 | ABS-G2030E – No TiO2 |
|---|---|---|---|
| 0 hour | 0.33 | -0.23 | 0.23 |
| 1 hour | 0.69 | 4.74 | 7.04 |
| 4 hour | 2.84 | 5.55 | 6.55 |

FIG. 22

TABLE 23

Percent Reduction

| | ABS-G2015H | ABS-G2020H | ABS-G2030H |
|---|---|---|---|
| 0 hour | 53.42% | -69.77% | 41.48% |
| 1 hour | 79.64% | 100.00% | 100.00% |
| 4 hour | 99.86% | 100.00% | 100.00% |

FIG. 23

Table 1. Surface Time-Kill Study Evaluating Four Coating Formulations Against Murine Norovirus: Time Zero Data

| Test Organism | Contact Time | Sample ID[a] | Viral Counts (TCID$_{50}$ per mL) | Log$_{10}$ Reduction | Percent Reduction |
|---|---|---|---|---|---|
| Murine norovirus | Time Zero | Formica - Ctrl | 1.48E+07 | N.A. | N.A. |
| | | SS-Ctrl | 6.76E+06 | | |

[a] SS: Stainless Steel

FIG. 24

Table 2. Surface Time-Kill Study Evaluating Four Coating Formulations Against Murine Norovirus:
4 Hour Contact Time Data

| Test Organism | Contact Time | Sample ID[a] | Viral Counts (TCID₅₀ per mL) | Log₁₀ Reduction | Percent Reduction |
|---|---|---|---|---|---|
| Murine norovirus | 4 Hours | Ctrl (Formica) | 1.00E+05 | N.A. | N.A. |
| | | Ctrl (SS) | 6.76E+04 | | |
| | | ABS-G2015 (SS) | 6.76E+04 | 0.00 | 0% |
| | | ABS-G2020 (Form) | ≤ 3.16E+03 | ≥ 1.50 | ≥ 97% |
| | | ABS-G2030 (Form) | 6.76E+03 | 1.00 | 90% |

[a] SS: Stainless Steel; SW: SurfaceWise; Form: Formica

[b] "≤": No viral cytopathology observed beyond toxic levels; therefore titer at or below limit of detection

FIG. 25

Table 3 Surface Time-Kill Study Evaluating Two Coating Formulations Against Murine Norovirus: 4 Hour Contact Time Data

| Test Organism | Contact Time | Sample ID* | Viral Counts (TCID₅₀ per mL) | Mean Viral Titer | Log₁₀ Reduction Relative to Time Zero | Percent Reduction Relative to Time Zero | Log₁₀ Reduction Relative to Timed Control | Percent Reduction Relative to Timed Control |
|---|---|---|---|---|---|---|---|---|
| Murine norovirus | 4 Hours | SS – Control (Rep A) | 8.76E+04 | 1.09E+05 | 1.47 | 97% | N.A. | N.A. |
| | | SS – Control (Rep B) | 1.48E+05 | | | | | |
| | | ABS-C2020 (Rep A) | 1.00E+04 | 1.57E+04 | 2.30 | 99.5% | 0.83 | 85.2% |
| | | ABS-C2020 (Rep B) | 2.14E+04 | | | | | |
| | | ABS-C2030 (Rep A) | 4.08E+03 | ≤ 3.92E+03 | ≥ 2.91 | ≥ 99.8% | ≥ 1.43 | ≥ 96.3% |
| | | ABS-C2030 (Rep B) | ≤ 3.16E+03 | | | | | |

*SS: Stainless Steel
"≤": Six viral replicates/dilutions observed and imparted toxic levels; therefore titer is at or below limit of detection

FIG. 26

Table 4 Surface Time-Kill Study Evaluating Two Coating Formulations Against Murine Norovirus: 6 Hour Contact Time Data

| Test Organism | Contact Time | Sample ID* | Viral Counts (TCID$_{50}$ per mL) | Mean Viral Titer | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|---|---|
| Murine norovirus | 6 Hours | SS - Control (Rep A) | 3.16E+04 | 4.96E+04 | 1.80 | 98% | N.A. | N.A. |
| | | SS - Control (Rep B) | 6.76E+04 | | | | | |
| | | ABS-G2020 (Rep A) | 1.00E+04 | 8.39E+03 | 2.48 | 99.7% | 0.77 | 83.1% |
| | | ABS-G2020 (Rep B) | 6.76E+03 | | | | | |
| | | ABS-G2030 (Rep A) | 4.68E+03 | ≤ 3.92E+03 | ≥ 2.91 | ≥ 99.6% | ≥ 1.10 | ≥ 92.1% |
| | | ABS-G2030 (Rep B) | ≤ 3.16E+03 | | | | | |

* SS: Stainless Steel
† ≤: No viral cytopathology observed beyond 10X levels; therefore titer at or below limit of detection

FIG. 27

| | | Untreated | | ABS-G2015E | | ABS-G2020E | | ABS-G2030E | |
|---|---|---|---|---|---|---|---|---|---|
| | | A | B | A | B | A | B | A | B |
| 0 hour | 1.E+04 | 3.08E+07 | 4.80E+06 | | | 2.58E+07 | 1.66E+07 | 2.10E+07 | 2.00E+07 |
| | 1.E+05 | 1.97E+08 | 2.30E+07 | 3.10E+07 | 4.10E+07 | 2.60E+07 | 3.40E+07 | 0.00E+00 | 0.00E+00 |
| | 1.E+01 | | | | | 8.00E+02 | 6.00E+02 | 0.00E+00 | 0.00E+00 |
| 1 hour | 1.E+02 | | | | | 1.00E+03 | 0.00E+00 | 0.00E+00 | 0.00E+00 |
| | 1.E+03 | | | 2.70E+06 | 3.80E+06 | 0.00E+00 | 0.00E+00 | 0.00E+00 | 0.00E+00 |
| | 1.E+04 | 2.90E+06 | 6.40E+06 | 1.63E+04 | | | | | |
| | 1.E+01 | | | 2.70E+04 | 6.20E+04 | 1.00E+02 | 0.00E+00 | 0.00E+00 | 0.00E+00 |
| 4 hour | 1.E+02 | | | 7.00E+04 | 8.00E+04 | 0.00E+00 | 0.00E+00 | 0.00E+00 | 0.00E+00 |
| | 1.E+03 | 2.70E+06 | 1.90E+05 | 2.00E+05 | 1.00E+05 | 0.00E+00 | 0.00E+00 | 0.00E+00 | 0.00E+00 |
| | 1.E+04 | 1.30E+07 | 1.70E+06 | | | 0.00E+00 | 0.00E+00 | 0.00E+00 | 0.00E+00 |

CFU/mL

FIG. 28

| | Log Reduction from Time Zero | | | |
|---|---|---|---|---|
| | Control | ABS-G2015E | ABS-G2020E | ABS-G2030E |
| 0 hour | N/A | 0.25 | 0.40 | 0.49 |
| 1 hour | 1.14 | 1.29 | 5.33 | 7.81 |
| 4 hour | 1.16 | 2.91 | 6.71 | 7.81 |

FIG. 29

| Percent Reduction from Time Zero | | | | |
|---|---|---|---|---|
| | Control | ABS-G2015E | ABS-G2020E | ABS-G2030E |
| 0 hour | N/A | 43.66% | 59.94% | 67.92% |
| 1 hour | 92.72% | 94.91% | 99.9995% | 99.999998% |
| 4 hour | 93.12% | 99.88% | 99.99998% | 99.999998% |

FIG. 30

CFU/mL

|  |  | Untreated | | ABS-G2015H | | ABS-G2020H | | ABS-G2030H | |
|---|---|---|---|---|---|---|---|---|---|
|  |  | A | B | A | B | A | B | A | B |
| 0 hour | 1.E+04 | 6.00E+05 | 4.00E+05 | 5.00E+05 | 4.00E+05 | 1.00E+06 | 8.00E+05 | 1.00E+05 | 1.00E+05 |
|  | 1.E+05 | 2.00E+06 | 2.00E+06 | 0.00E+00 | 0.00E+00 | 0.00E+00 | 1.00E+06 | 0.00E+00 | 0.00E+00 |
|  | 1.E+01 |  |  |  |  |  |  |  |  |
|  | 1.E+02 |  |  |  |  |  |  |  |  |
| 1 hour | 1.E+03 | 9.00E+05 | 1.58E+06 | 9.10E+05 | 6.70E+05 | 2.00E+05 | 5.70E+05 | 0.00E+00 | 0.00E+00 |
|  | 1.E+04 | 1.40E+06 | 1.70E+06 | 1.20E+06 | 3.00E+05 | 2.00E+05 | 9.00E+05 | 0.00E+00 | 0.00E+00 |
|  | 1.E+05 | 0.00E+00 | 0.00E+00 | 4.00E+06 | 0.00E+00 | 0.00E+00 | 0.00E+00 | 0.00E+00 | 0.00E+00 |
|  | 1.E+01 |  |  |  |  |  |  |  |  |
|  | 1.E+02 |  |  |  |  |  |  |  |  |
| 4 hour | 1.E+03 | 1.28E+06 | 4.80E+05 | 1.00E+04 | 4.00E+04 | 0.00E+00 | 0.00E+00 | 0.00E+00 | 0.00E+00 |
|  | 1.E+04 | 8.00E+05 | 4.00E+05 | 0.00E+00 | 0.00E+00 | 0.00E+00 | 0.00E+00 | 0.00E+00 | 0.00E+00 |
|  | 1.E+05 | 1.00E+06 | 1.00E+06 | 0.00E+00 | 0.00E+00 | 0.00E+00 | 0.00E+00 | 0.00E+00 | 0.00E+00 |

FIG. 31

| | ABS-G2015H | ABS-G2020H | ABS-G2030H |
|---|---|---|---|
| 0 hour | 0.74 | 0.25 | 1.40 |
| 1 hour | -0.10 | 0.47 | 5.97 |
| 4 hour | 2.00 | 5.92 | 5.92 |

Log Reduction

FIG. 32

| | Percent Reduction | | |
|---|---|---|---|
| | ABS-G2015H | ABS-G2020H | ABS-G2030H |
| 0 hour | 82.00% | 44.00% | 96.00% |
| 1 hour | -26.88% | 66.49% | 100.00% |
| 4 hour | 98.99% | 100.00% | 100.00% |

| Data from | 2015T | | | | 2015AO1T | | | | 2015 2020AO1T (5:1:1) | | | | 2015 2020AO1T (5:2:1) | | | |
|---|---|---|---|---|---|---|---|---|---|---|---|---|---|---|---|---|
| | Fresh | | Rinsed | Worn (x30) | Fresh | | Rinsed | Worn (x30) | Fresh | | Rinsed | Worn (x30) | Fresh | | Rinsed | Worn (x30) |
| | Weight percent remaining (%) | | | | | | | | | | | | | | | |
| PR63 | 100 | | N/A | 61.20 | 100 | | N/A | 61.69 | 100 | | N/A | 67.04 | 100 | | N/A | 76.50 |

| STUDY NO. | Weight Percent remaining (%) | | | | | | | | | | | |
|---|---|---|---|---|---|---|---|---|---|---|---|---|
| | 2015T | | | 2015A01T | | | 20152020A01T (5:1:1) | | | 20152020A01T (5:2:1) | | |
| | Fresh | Rinse | Worn (x10) | Fresh | Rinse | Worn (x10) | Fresh | Rinse | Worn (x10) | Fresh | Rinse | Worn (x10) |
| PR59 | | | | 100.00 | 60.73 | 74.38 | | | | | | |
| PR60 | | | | 100.00 | 54.11 | 66.91 | | | | | | |
| PR66 | 100.00 | 40.56 | 80.47 | 100.00 | 31.17 | 75.17 | 100.00 | 46.06 | 59.49 | | | |
| PR67 | 100.00 | 53.23 | 82.35 | 100.00 | 50.00 | 78.23 | 100.00 | 49.28 | 66.42 | | | |
| PR68 | 100.00 | 61.32 | 73.96 | 100.00 | 61.26 | 65.69 | | | | 100.00 | 65.66 | 73.74 |
| PR69 | 100.00 | 32.93 | 76.32 | 100.00 | 35.90 | 71.05 | | | | 100.00 | 44.76 | 78.02 |
| PR70-1 | | | | | | | | | | 100.00 | 48.81 | 89.29 |
| PR70-2 | | | | | | | | | | 100.00 | 61.80 | 78.21 |
| PR70-3 | | | | | | | | | | 100.00 | 35.87 | 84.31 |
| PR70-4 | | | | | | | | | | 100.00 | 47.54 | 86.27 |
| PR70-5 | | | | | | | | | | 100.00 | 55.30 | 75.76 |
| PR71-1 | | | | | | | | | | 100.00 | 59.09 | 94.38 |
| PR71-2 | | | | | | | | | | 100.00 | 50.65 | 79.17 |
| PR71-3 | | | | | | | | | | 100.00 | 40.86 | 81.32 |
| PR71-4 | | | | | | | | | | 100.00 | 52.78 | 80.19 |
| PR71-5 | | | | | | | | | | 100.00 | 53.72 | 76.52 |
| PR72-1 | | | | | | | | | | 100.00 | 65.42 | 65.84 |
| PR72-2 | | | | | | | | | | 100.00 | 65.14 | 67.88 |
| PR72-3 | | | | | | | | | | 100.00 | 62.40 | 78.40 |
| PR72-4 | | | | | | | | | | 100.00 | 64.83 | 74.83 |
| PR72-5 | | | | | | | | | | 100.00 | 58.04 | 72.83 |
| PR73-1 | | | | | | | | | | 100.00 | 72.97 | 70.80 |
| PR73-2 | | | | | | | | | | 100.00 | 64.49 | 65.42 |
| PR73-3 | | | | | | | | | | 100.00 | 58.20 | 66.60 |
| PR73-4 | | | | | | | | | | 100.00 | 66.78 | 67.01 |
| PR73-5 | | | | | | | | | | 100.00 | 68.31 | 81.04 |
| PR88 | | | | | | | | | | 100.00 | 36.27 | 62.84 |
| PR89 | | | | | | | | | | 100.00 | 41.65 | 62.21 |
| PR90 | | | | | | | | | | 100.00 | 67.61 | 101.77 |
| Average | 100.00 | 47.01 | 78.28 | 100.00 | 48.86 | 71.91 | 100.00 | 47.67 | 62.96 | 100.00 | 56.36 | 76.59 |

FIG. 35

| Composition Used | Weight Percent Remaining | | |
| --- | --- | --- | --- |
| | Fresh | Rinsed | Worn (x10) |
| 2015T | 100.00 | 47.01 | 78.28 |
| 2015A01T | 100.00 | 48.86 | 71.91 |
| 20152020A01T (5:2:1) | 100.00 | 56.36 | 76.59 |

E. coli 25922

| Study | 2015T | | | 2015A01T | | | 20152020A01T (5:1:1) | | | 20152020A01T (5:2:1) | | |
|---|---|---|---|---|---|---|---|---|---|---|---|---|
| | Fresh | Rinse | Wornx10 | Fresh | Rinse | Wornx10 | Fresh | Rinse | Wornx10 | Fresh | Rinse | Wornx10 |
| PR53 | | | | 1.63 | 0.65 | | | | | | | |
| PR57 | | | | 1.65 | 0.76 | | | | | | | |
| PR59 | | | | 2.04 | 0.76 | | | | | | | |
| PR62 | | | | 0.45 | | 0.05 | | | | | | |
| PR63 | 0.69 | | | 0.41 | | | 1.01 | | | 0.64 | | |
| PR66 | 1.35 | 0.39 | 0.47 | 1.89 | 0.47 | 0.96 | 2.85 | 0.78 | 1.03 | | | |
| PR68 | 0.71 | 0.19 | 0.76 | 0.75 | 0.28 | 0.72 | | | | 1.28 | 0.61 | 0.67 |
| PR70-1 | | | | | | | | | | 1.32 | 0.5 | 0.96 |
| PR70-2 | | | | | | | | | | 0.98 | 0.42 | 0.70 |
| PR70-3 | | | | | | | | | | 1.27 | 0.28 | 1.15 |
| PR70-4 | | | | | | | | | | 1.16 | 0.15 | 0.96 |
| PR70-5 | | | | | | | | | | 0.73 | 0 | 0.93 |
| PR72-1 | | | | | | | | | | 0.75 | 0.78 | 0.89 |
| PR72-2 | | | | | | | | | | 0.55 | 0.46 | 0.51 |
| PR72-3 | | | | | | | | | | 0.62 | 0.34 | 0.59 |
| PR72-4 | | | | | | | | | | 0.62 | 0.3 | 0.79 |
| PR72-5 | | | | | | | | | | 1.01 | 0.35 | 1.21 |
| PR77 | | | | | | | | | | 1.14 | | |
| PR79 | | | | | | | | | | 0.81 | | |
| PR83 | | | | | | | | | | 0.83 | | |
| PR88 | | | | | | | | | | 1.36 | 1.18 | 0.41 |
| Average | 0.92 | 0.29 | 0.62 | 1.26 | 0.58 | 0.58 | 1.93 | 0.78 | 1.03 | 0.94 | 0.45 | 0.81 |

| | Fresh | Rinse | Worn (x10) |
|---|---|---|---|
| 2015T | 0.92 | 0.29 | 0.62 |
| 2015A01T | 1.26 | 0.58 | 0.58 |
| 20152020A01T (5:2:1) | 0.94 | 0.45 | 0.81 |

FIG. 37

S. epidermidis 12228

| Study | Test organism: S. epidermidis 12228 ||||||||||||
| | 2015T ||| 2015A01T ||| 20152020A01T (5:1:1) ||| 20152020A01T (5:2:1) |||
| | Fresh | Rinse | Wornx10 | Fresh | Rinse | Wornx10 | Fresh | Rinse | Wornx10 | Fresh | Rinse | Wornx10 |
|---|---|---|---|---|---|---|---|---|---|---|---|---|
| PR55 | | | | 0.36 | 0 | | | | | | | |
| PR58 | | | | 0.24 | 0.32 | | | | | | | |
| PR60 | | | | 1.12 | 0 | | | | | | | |
| PR61 | | | | 0.68 | | 0.08 | | | | | | |
| PR64 | 0.17 | | | 0.36 | | | 0.04 | | | 0.03 | | |
| PR67 | 0.22 | 0.06 | 0.17 | 0.07 | 0.01 | 0.13 | 0.16 | 0.02 | 0.22 | | | |
| PR69 | 0.27 | 0.12 | 0.26 | 0.12 | 0 | 0.03 | | | | 0.6 | 0.51 | 0.11 |
| PR71-1 | | | | | | | | | | 0.14 | 0.37 | 0.28 |
| PR71-2 | | | | | | | | | | 0.08 | 0.05 | 0.19 |
| PR71-3 | | | | | | | | | | 0.37 | 0.20 | 0.19 |
| PR71-4 | | | | | | | | | | 0.21 | 0.19 | 0.18 |
| PR71-5 | | | | | | | | | | 0.12 | 0.03 | 0.11 |
| PR73-1 | | | | | | | | | | 0 | 0 | 0.19 |
| PR73-2 | | | | | | | | | | 0.25 | 0.17 | 0.09 |
| PR73-3 | | | | | | | | | | 0 | 0.35 | 0.48 |
| PR73-4 | | | | | | | | | | 0.47 | 0.42 | 0.37 |
| PR73-5 | | | | | | | | | | 0.32 | 0.13 | 0.12 |
| PR78 | | | | | | | | | | 0.29 | | |
| PR80 | | | | | | | | | | 0.58 | | |
| PR82 | | | | | | | | | | 0.28 | | |
| PR89 | | | | | | | | | | 1.12 | 0.15 | 1.38 |
| PR92 | | | | | | | | | | 0.58 | | 0.52 |
| Average | 0.22 | 0.09 | 0.22 | 0.42 | 0.07 | 0.08 | 0.10 | 0.02 | 0.22 | 0.32 | 0.21 | 0.32 |

| | Fresh | Rinse | Worn (x 10) |
|---|---|---|---|
| 2015T | 0.22 | 0.09 | 0.22 |
| 2015A01T | 0.42 | 0.07 | 0.08 |
| 20152020A01T (5:2:1) | 0.32 | 0.21 | 0.32 |

FIG. 38

TABLE 24

| Test Organism | Contact Time | Sample ID | Cfu/mL | Mean Cfu/mL | Log₁₀ Reduction | Percent Reduction |
|---|---|---|---|---|---|---|
| E. coli | 0 hour | Control A | 2.50E+07 | 2.13E+07 | 0.00 | 0% |
| | | Control B | 1.75E+07 | | | |
| | | Choline Chloride A | 2.15E+07 | 2.58E+07 | -0.08 | -21% |
| | | Choline Chloride B | 3.00E+07 | | | |
| | | Choline Bitartrate A | 1.80E+07 | 1.40E+07 | 0.18 | 34% |
| | | Choline Bitartrate B | 1.00E+07 | | | |
| | | Acetylcholine Chloride A | 1.45E+07 | 1.20E+07 | 0.25 | 44% |
| | | Acetylcholine Chloride B | 9.50E+06 | | | |

FIG. 40

TABLE 25

| Test Organism | Contact Time | Sample ID | Cfu/mL | Mean Cfu/mL | Log₁₀ Reduction | Percent Reduction |
|---|---|---|---|---|---|---|
| E. coli | 1 hour | Control A | 1.10E+07 | 7.40E+06 | 0.00 | 0% |
| | | Control B | 3.80E+06 | | | |
| | | Choline Chloride A | 7.38E+04 | 2.92E+05 | 1.40 | 96.06% |
| | | Choline Chloride B | 5.10E+05 | | | |
| | | Choline Bitartrate A | 5.75E+04 | 3.03E+04 | 2.39 | 99.59% |
| | | Choline Bitartrate B | 3.17E+03 | | | |
| | | Acetylcholine Chloride A | 1.44E+04 | 1.05E+05 | 1.85 | 98.59% |
| | | Acetylcholine Chloride B | 1.95E+05 | | | |

FIG. 41

TABLE 26

| Test Organism | Contact Time | Sample ID | Cfu/mL | Mean Cfu/mL | Log₁₀ Reduction | Percent Reduction |
|---|---|---|---|---|---|---|
| E. coli | 0 hour | Control A | 1.45E+07 | 1.34E+07 | 0.00 | 0% |
| | | Control B | 1.22E+07 | | | |
| | | ABS-2040 A | 1.05E+07 | 1.05E+07 | 0.10 | 21% |
| | | ABS-2040 B | 1.05E+07 | | | |
| | | ABS-2041 A | 1.10E+07 | 9.75E+06 | 0.14 | 27% |
| | | ABS-2041 B | 8.50E+06 | | | |

FIG. 42

TABLE 27

| Test Organism | Contact Time | Sample ID | Cfu/mL | Mean Cfu/mL | Log$_{10}$ Reduction | Percent Reduction |
|---|---|---|---|---|---|---|
| E. coli | 1 hour | Control A | 7.70E+06 | 7.45E+06 | 0.00 | 0% |
| | | Control B | 7.20E+06 | | | |
| | | ABS-2040 A | 5.10E+03 | 3.28E+03 | 3.36 | 99.96% |
| | | ABS-2040 B | 1.45E+03 | | | |
| | | ABS-2041 A | 1.34E+03 | 3.13E+03 | 3.38 | 99.96% |
| | | ABS-2041 B | 4.91E+03 | | | |

FIG. 43

TABLE 28

| Test Organism | Contact Time | Sample ID | Cfu/mL | Mean Cfu/mL | Log₁₀ Reduction | Percent Reduction |
|---|---|---|---|---|---|---|
| E. coli | 4 hour | Control A | 3.30E+06 | 3.95E+06 | 0.00 | 0% |
| | | Control B | 4.60E+06 | | | |
| | | ABS-2040 A | 1.00E+00 | 1.00E+00 | 6.60 | 99.999987% |
| | | ABS-2040 B | 1.00E+00 | | | |
| | | ABS-2041 A | 1.00E+00 | 1.00E+00 | 6.60 | 99.999987% |
| | | ABS-2041 B | 1.00E+00 | | | |

FIG. 44

TABLE 29

| Test Organism | Contact Time | Sample ID | Cfu/mL | Mean Cfu/mL | Log₁₀ Reduction | Percent Reduction |
|---|---|---|---|---|---|---|
| E. coli | 0 hour | Control A | 1.35E+07 | 2.35E+07 | 0.00 | 0% |
| | | Control B | 3.35E+07 | | | |
| | | ABS-2040 A | 6.00E+06 | 6.75E+06 | 0.54 | 71% |
| | | ABS-2040 B | 7.50E+06 | | | |
| | | ABS-2041 A | 2.40E+06 | 1.32E+07 | 0.25 | 44% |
| | | ABS-2041 B | 2.40E+07 | | | |

FIG. 45

TABLE 30

| Test Organism | Contact Time | Sample ID | Cfu/mL | Mean Cfu/mL | Log₁₀ Reduction | Percent Reduction |
|---|---|---|---|---|---|---|
| E. coli | 1 hour | Control A | 1.07E+07 | 1.30E+07 | 0.00 | 0% |
| | | Control B | 1.54E+07 | | | |
| | | ABS-2040 A | 1.00E+02 | 6.13E+03 | 3.33 | 99.95% |
| | | ABS-2040 B | 1.22E+04 | | | |
| | | ABS-2041 A | 5.00E+02 | 2.80E+04 | 2.67 | 99.8% |
| | | ABS-2041 B | 5.56E+04 | | | |

FIG. 46

TABLE 31

| Test Organism | Contact Time | Sample ID | Cfu/mL | Mean Cfu/mL | Log$_{10}$ Reduction | Percent Reduction |
|---|---|---|---|---|---|---|
| E. coli | 4 hour | Control A | 4.30E+06 | 4.00E+06 | 0.00 | 0% |
| | | Control B | 3.70E+06 | | | |
| | | ABS-2040 A | 1.00E+00 | 2.55E+01 | 5.20 | 99.9998% |
| | | ABS-2040 B | 5.00E+01 | | | |
| | | ABS-2041 A | 1.00E+00 | 2.55E+01 | 5.20 | 99.9998% |
| | | ABS-2041 B | 5.00E+01 | | | |

FIG. 47

ANTIMICROBIAL COATINGS COMPRISING QUATERNARY SILANES

CROSS-REFERENCE TO RELATED APPLICATIONS

This application is a continuation-in-part of U.S. application Ser. No. 15/432,413, filed Feb. 14, 2017 entitled "METHODS OF PREPARING SELF-DECONTAMINATING SURFACES USING REACTIVE SILANES, TRIETHANOLAMINE AND TITANIUM ANATASE SOL." The '413 application is a continuation of U.S. application Ser. No. 15/041,974, filed Feb. 11, 2016 entitled "ANTIMICROBIAL COATING AND METHOD TO FORM SAME" (now U.S. Pat. No. 9,918,475). The '974 application claims priority to U.S. Provisional Patent Application Ser. No. 62/114,998, filed Feb. 11, 2015 entitled "ANTIMICROBIAL COATING AND METHOD TO FORM SAME." The '974 application is a continuation-in-part of U.S. application Ser. No. 14/932,840, filed Nov. 4, 2015 entitled "COMPOSITION AND METHOD TO FORM A SELF DECONTAMINATING SURFACE" (now U.S. Pat. No. 9,856,360). The '840 application claims priority to U.S. Provisional Patent Application Ser. No. 62/075,020, filed Nov. 4, 2014 entitled "COMPOSITION AND METHOD TO FORM A SELF DECONTAMINATING SURFACE." All of these disclosures are incorporated herein by reference in their entireties for all purposes.

FIELD

The present disclosure relates generally to antimicrobial coating compositions and methods of forming same, and methods of improving the durability of quaternary silane coatings on surfaces.

BACKGROUND

In a publication entitled "Evaluation of Two Organosilane Products for Sustained Antimicrobial Activity on High-Touch Surfaces in Patient Rooms, American Journal of Infection Control 42 (2014) 326-8, reports, inter alia, "To the best of our knowledge, ours is the first published controlled trial of applying organosilane compounds to high-touch surfaces in patient rooms as a strategy for reducing the level of microbial contamination of environmental surfaces between daily cleanings." Id. at 327.

The authors found the two organosilanes ineffective for any sort of sustained antimicrobial efficacy. "In conclusion, our study was not able to demonstrate sustained antimicrobial activity for either organosilane product tested when applied to high-touch surfaces." Id. at 328.

SUMMARY

In various embodiments of the present disclosure, a method of forming an antimicrobial coating on a portion of a surface is described. The method generally comprises coating a portion of a surface with (1) a composition comprising at least one organosilane and at least one amine, and (2) a composition comprising a titanyl sol-gel. In certain aspects, both of these compositions are aqueous compositions. The two compositions may be applied to a portion of a surface in either order, or applied simultaneously such as from two spray nozzles directed to the same portion of the surface.

In general embodiments, the at least one organosilane is selected from the group consisting of 3-(trihydroxysilyl)propyl dimethyloctadecyl ammonium chloride, dimethyloctadecyl 3-(trimethoxysilyl)propyl ammonium chloride, 3-chloropropyltrimethoxysilane, and mixtures thereof. In various embodiments, the titanyl sol-gel comprises an aqueous mixture of peroxotitanium acid and peroxo-modified anatase sol.

In various embodiments, addition of 3-chloropropyltrimethoxysilane to a composition of 3-(trihydroxysilyl)propyl dimethyloctadecyl ammonium chloride and triethanolamine improves the storage stability of the aqueous mixture of quaternary silane and amine.

In various embodiments, addition of 3-chloropropyltrimethoxysilane to a composition of 3-(trihydroxysilyl)propyl dimethyloctadecyl ammonium chloride and triethanolamine improves the durability of the resulting coating compared to a coating of 3-(trihydroxysilyl)propyl dimethyloctadecyl ammonium chloride and triethanolamine alone, and consequently, extends the antimicrobial efficacy of the coating.

In various embodiments, a method of preparing an antimicrobial coating on a portion of a surface comprises: disposing an aqueous antimicrobial coating composition comprising 3-(trihydroxysilyl)propyl dimethyloctadecyl ammonium chloride and triethanolamine on the portion of the surface; and disposing an aqueous titanyl sol-gel on the portion of the surface overtop of the aqueous antimicrobial coating composition. In various examples, the antimicrobial coating thus formed exhibits residual antimicrobial efficacy against *E. coli* 25922 and *S. epidermidis* 12228. In various examples, durability of a coating was assessed by repeated abrasion of coated test coupons in a straight-line washability machine, measuring percent weight loss from the coating and/or residual antimicrobial efficacy of the worn coatings. In other examples, coatings were exposed to water rinsing prior to weight loss measurements and antimicrobial efficacy assessments.

In various embodiments, the titanyl sol-gel comprises 0.85 wt. % peroxotitanium acid and peroxo-modified anatase sol mixture, with the remainder of the sol-gel being water.

In certain aspects, the aqueous antimicrobial coating composition comprises from about 0.5 wt. % to about 1.0 wt. % 3-(trihydroxysilyl)propyl dimethyloctadecyl ammonium chloride, and from about 0.01 wt. % to about 0.10 wt. % triethanolamine, with the remainder of the composition being water.

In certain examples, the aqueous antimicrobial coating composition further comprises 3-chloropropyltrimethoxysilane. In a more specific example, an aqueous antimicrobial coating composition comprises about 0.75 wt. % 3-(trihydroxysilyl)propyl dimethyloctadecyl ammonium chloride, about 0.06 wt. % 3-chloropropyltrimethoxysilane, and about 0.045 wt. % triethanolamine, with the remainder of the composition being water.

In variations of the method of forming an antimicrobial coating, an aqueous antimicrobial coating composition comprises about 0.75 wt. % 3-(trihydroxysilyl)propyl dimethyloctadecyl ammonium chloride, about 0.12 wt. % 3-chloropropyltrimethoxysilane, and about 0.045 wt. % triethanolamine, with the remainder of the composition being water.

In various embodiments, a method of preparing an antimicrobial coating on a portion of a surface comprises: spray coating an aqueous antimicrobial coating composition comprising about 0.75 wt. % 3-(trihydroxysilyl)propyl dimethyloctadecyl ammonium chloride, about 0.06 wt. % 3-chloropropyltrimethoxysilane, and about 0.045 wt. % triethanolamine, remainder water, on the portion of the surface; allowing the aqueous antimicrobial coating composition to visibly dry on the portion of the surface; disposing an aqueous titanyl sol-gel comprising about 0.85 wt. % of a mixture of peroxotitanium acid and peroxo-modified anatase sol in water on the portion of the surface overtop of the dried aqueous antimicrobial coating composition; and allowing the aqueous sol-gel to dry to form the antimicrobial coating. The resulting antimicrobial coating exhibits residual antimicrobial efficacy against E. coli and S. epidermidis after water rinsing or abrasion.

In various embodiments, a method of preparing an antimicrobial coating on a portion of a surface comprises: spray coating an aqueous antimicrobial coating composition comprising about 0.75 wt. % 3-(trihydroxysilyl)propyl dimethyloctadecyl ammonium chloride, about 0.12 wt. % 3-chloropropyltrimethoxysilane, and about 0.045 wt. % triethanolamine, remainder water, on the portion of the surface; allowing the aqueous antimicrobial coating composition to visibly dry on the portion of the surface; disposing an aqueous titanyl sol-gel comprising about 0.85 wt. % of a mixture of peroxotitanium acid and peroxo-modified anatase sol in water on the portion of the surface overtop of the dried aqueous antimicrobial coating composition; and allowing the aqueous sol-gel to dry to form the antimicrobial coating. The resulting antimicrobial coating exhibits residual antimicrobial efficacy against E. coli and S. epidermidis after water rinsing or abrasion.

BRIEF DESCRIPTION OF THE DRAWINGS

The disclosure will be better understood from a reading of the following detailed description taken in conjunction with the drawings in which like reference designators are used to designate like elements, and in which:

FIG. 5 sets for the test methods used for each of the organisms Clostridium difficile, methicillin-resistant Staphylococcus aureus (MRSA), vancomycin-resistant Enterococcus (VRE), and carbapenem-resistant Enterobacteriaceae (CRE), in accordance with various embodiments;

FIG. 6 sets forth the average number of total bacteria detected per 100 cm$^2$ at all locations and percent reductions in total bacterial numbers after treatment, in accordance with various embodiments;

FIG. 7 shows the reduction in bacteria at 1, 2, 4, 8, and 15 weeks after treatment, as compared to before treatment, in accordance with various embodiments;

FIG. 8 shows the percent of samples in which antibiotic resistant bacteria were isolated at the different sites sampled, in accordance with various embodiments;

FIG. 9 shows efficacy data for the treated coupons after inoculation with E co/i, in accordance with various embodiments;

FIG. 10 shows efficacy data. for the treated coupons after inoculation with MS-2, in accordance with various embodiments:

FIG. 11 shows efficacy data for the treated coupons after inoculation with MRSA, in accordance with various embodiments;

FIG. 12 shows efficacy data for the treated coupons after inoculation with E. coli, in accordance with various embodiments;

FIG. 13 shows efficacy data for the treated coupons after inoculation with MS-2, in accordance with various embodiments;

FIG. 14 shows efficacy data for the treated coupons after inoculation with MRSA, in accordance with various embodiments;

FIG. 15 shows efficacy data for coupons treated with 3-aminopropyltrimethoxy silane and Applicants' Titanium Oxide Moieties after inoculation with E. coli, in accordance with various embodiments;

FIG. 16 shows efficacy data for coupons treated with 3-aminopropyltrimethoxy silane and Applicants' Titanium Oxide Moieties after inoculation with E. coli, in accordance with various embodiments;

FIG. 17 shows efficacy data for coupons treated with 3-aminopropyltrimethoxy silane and Applicants' Titanium Oxide Moieties after inoculation with E. coli, in accordance with various embodiments;

FIG. 18 shows efficacy data for coupons treated with 3-chloropropyltrimethoxy silane and Applicants' Titanium Oxide Moieties after inoculation with E. coli, in accordance with various embodiments;

FIG. 19 shows efficacy data for coupons treated with 3-chloropropyltrimethoxy silane and Applicants' Titanium Oxide Moieties after inoculation with E. coli, in accordance with various embodiments;

FIG. 20 shows efficacy data for coupons treated with 3-chloropropyltrimethoxy silane and Applicants' Titanium Oxide Moieties after inoculation with E. coli, in accordance with various embodiments;

FIG. 21 shows CFU/mL data for each of the three coating formulations, wherein each formulation did not include one or more titanium-oxide moieties, in accordance with various embodiments;

FIG. 22 shows Log Reduction data for the three formulations evaluated, wherein each formulation did not include one or more titanium-oxide moieties, in accordance with various embodiments;

FIG. 23 shows Percent Reduction data for the three formulations utilized, wherein each formulation did not include one or more titanium-oxide moieties, in accordance with various embodiments;

FIG. 24 shows beginning viral counts for murine norovirus on Formica and stainless steel coupons (time zero data), in accordance with various embodiments;

FIG. 25 shows surface time-kill data for four coatings against murine norovirus, in accordance with various embodiments;

FIG. 26 shows surface time-kill data for four coatings against murine norovirus, in accordance with various embodiments;

FIG. 27 shows surface time-kill data for four coatings against murine norovirus, in accordance with various embodiments;

FIGS. 28-30 set forth antimicrobial efficacy data for electrostatic sprayed coatings, in accordance with various embodiments;

FIGS. 31-33 set forth antimicrobial efficacy data for conventionally sprayed coatings, in accordance with various embodiments;

FIG. 34 sets forth weight loss data for various coatings subjected to 30-cycles of abrasion in an in-line washability machine, in accordance with various embodiments;

FIG. 35 sets forth weight loss data for various coatings subjected to rinsing or subjected to 10-cycles of abrasion in an in-line washability machine, in accordance with various embodiments;

FIG. 37 sets forth raw and averaged antimicrobial efficacy results against *E. coli* 25922 on various coatings previously subjected to rinsing or to 10-cycles of abrasion in an in-line washability machine;

FIG. 38 sets forth raw and averaged antimicrobial efficacy results against *S. epidermidis* 12228 on various coatings previously subjected to rinsing or to 10-cycles of abrasion in an in-line washability machine;

FIG. 40 shows antimicrobial efficacy data for the choline formulations immediately after inoculation, in accordance with various embodiments FIG. 41 shows antimicrobial efficacy data for the choline formulations 1-hour after inoculation, in accordance with various embodiments;

FIG. 42 shows antimicrobial efficacy data for the choline formulations immediately after inoculation, in accordance with various embodiments;

FIG. 43 shows antimicrobial efficacy data for the choline formulations 1-hour after inoculation, in accordance with various embodiments;

FIG. 44 shows antimicrobial efficacy data for the choline formulations 4-hours after inoculation, in accordance with various embodiments;

FIG. 45 shows antimicrobial efficacy data for the choline formulations immediately after inoculation, in accordance with various embodiments;

FIG. 46 shows antimicrobial efficacy data for the choline formulations 1-hour after inoculation, in accordance with various embodiments; and FIG. 47 shows antimicrobial efficacy data for the choline formulations 4-hours after inoculation, in accordance with various embodiments.

DETAILED DESCRIPTION

Figure 1:
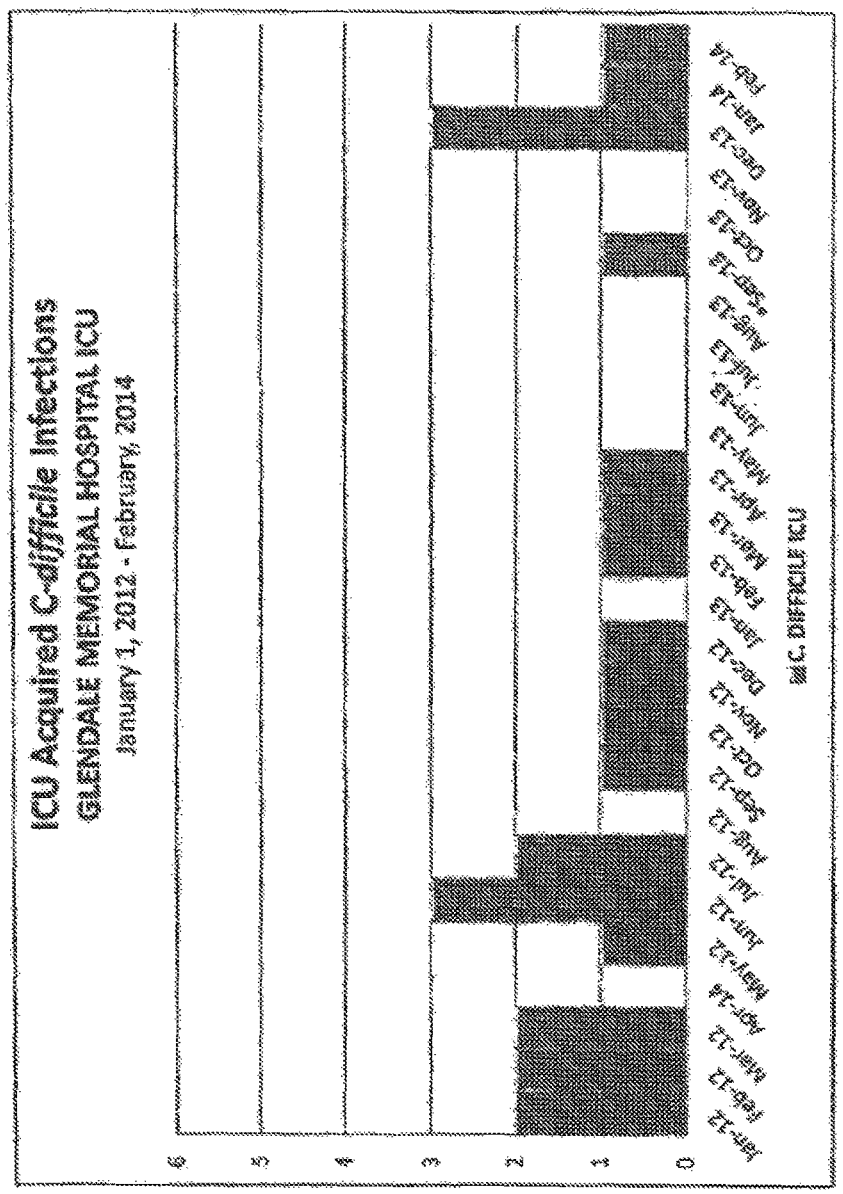
FIG. 1 graphically shows the number of hospital acquired C-difficile infections in the Glendale Memorial Hospital ICU from January 2012 through February 2014, in accordance with various embodiments.

The disclosure is described in exemplary embodiments in the following description with reference to the Figures, in which like numbers represent the same or similar elements. Reference throughout this specification to "one embodiment," "preferred embodiments", "an embodiment," "various embodiments" or similar language means that a particular feature, structure, or characteristic described in connection with the embodiment is included in various embodiments of the present disclosure, but the feature, structure, or characteristic may be included in any of the embodiments.

The described features, structures, or characteristics of the disclosure may be combined in any suitable manner in various embodiments. In the following description, numerous specific details are recited to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

As used herein, the term "antimicrobial" is used generally to indicate at least some level of microbe kill by a composition or a coating on a portion of a surface. For example, antimicrobial may be used to indicate a biostatic efficacy, sanitizing level (3-log, or 99.9%) reduction in at least one organism, or a disinfection level (5-log, or 99.999%) reduction in at least one organism, or sterilization (no detectable organisms). Microbes, or microorganisms, may include any species of bacteria, virus, mold, yeast, or spore. The terms "residual antimicrobial," "residual self-sanitizing," and "self-decontaminating surface" are used interchangeably to indicate a hard or soft surface that maintains antimicrobial efficacy over a certain period of time under certain conditions once the surface is coated with an antimicrobial coating composition. A coated surface may maintain residual antimicrobial efficacy indefinitely, or the coating may eventually "wear out" and lose its residual antimicrobial efficacy. An antimicrobial coating composition may function as a contact sanitizer, bacteriostatic material, disinfectant, or sterilant, (e.g. as a liquid antimicrobial applied to a contaminated surface) and also have the ability to leave behind a residual antimicrobial coating on the surface once dried or cured thereon that can keep inactivating new microorganisms that contact the coated surface. In various embodiments, coating compositions may not be antimicrobial until dried or cured on a surface, but are still referred to as antimicrobial coating compositions because of their ability to produce a residual antimicrobial coating on a surface. Antimicrobial coating compositions for use in various embodiments may provide a residual antimicrobial efficacy to a surface, meaning that a microorganism later inoculated on or that otherwise comes in contact with the coated surface may experience cell death, destruction, or inactivation. The residual antimicrobial effect made possible by the coatings is not limited by a particular mechanism of action, and no such theories are proffered. For example, an antimicrobial effect measured on a surface may be the result of intracellular mutations, inhibition of certain cellular processes, rupture of a cell wall, or a nondescript inactivation of the organism. Other antimicrobial effects may include inhibiting the reproduction of an organism, or inhibiting the organism's ability to accumulate into biofilms.

As used herein, the term "antimicrobial coating composition" refers to a chemical composition comprising at least one chemical species, which is used to produce a residual antimicrobial coating on a surface after the composition is applied and then either dried, allowed to dry, or cured in some manner. However, the term is extended to include a composition that may be applied sequentially (e.g. over or under) or contemporaneously with the application of an antimicrobial coating composition comprising an antimicrobial active, such as to assist in bonding the residual antimicrobial coating to the surface, improve durability of the overall coating, and/or to provide a catalytic effect or some sort of potentiation or synergy with the residual antimicrobial coating comprising an antimicrobial active. For simplicity herein, each one of multiple compositions used sequentially or contemporaneously to produce an overall residual antimicrobial coating on a portion of a surface is referred to as an "antimicrobial coating composition," even if one or more of the compositions used for coating has no identifiable antimicrobial active or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In other embodiments, chemical constituents within an antimicrobial coating composition may chemically react on the surface that the composition is applied to, such as while the composition is drying and concentrating on the surface or while the coating composition is cured by various methods. Antimicrobial coating compositions for use in various embodiments may further comprise any number and combination of inert excipients, such as for example, solvents, buffers, acids, alkali, surfactants, emulsifiers, stabilizers, thickeners, free-radical initiators, catalysts, etc.

In various embodiments of Applicants' composition and method, a coating is formed on a surface of an object, where that coating comprises a plurality of titanium-oxygen bonds, where that coating is formed by disposing on the surface a mixture of Peroxotitanium acid solution and Peroxo-modified anatase sol (collectively "Titanium-Oxygen Moieties").

In various embodiments, Applicants' Titanium-Oxygen Moieties comprises up to about a total of one weight percent loading of the mixture of Peroxotitanium acid solution and Peroxo-modified anatase sol. In various embodiments, Applicants' Titanium-Oxygen Moieties comprises about 0.5 weight percent Peroxotitanium acid solution in combination with about 0.5 weight percent Peroxo-modified anatase sol.

Figure 4:
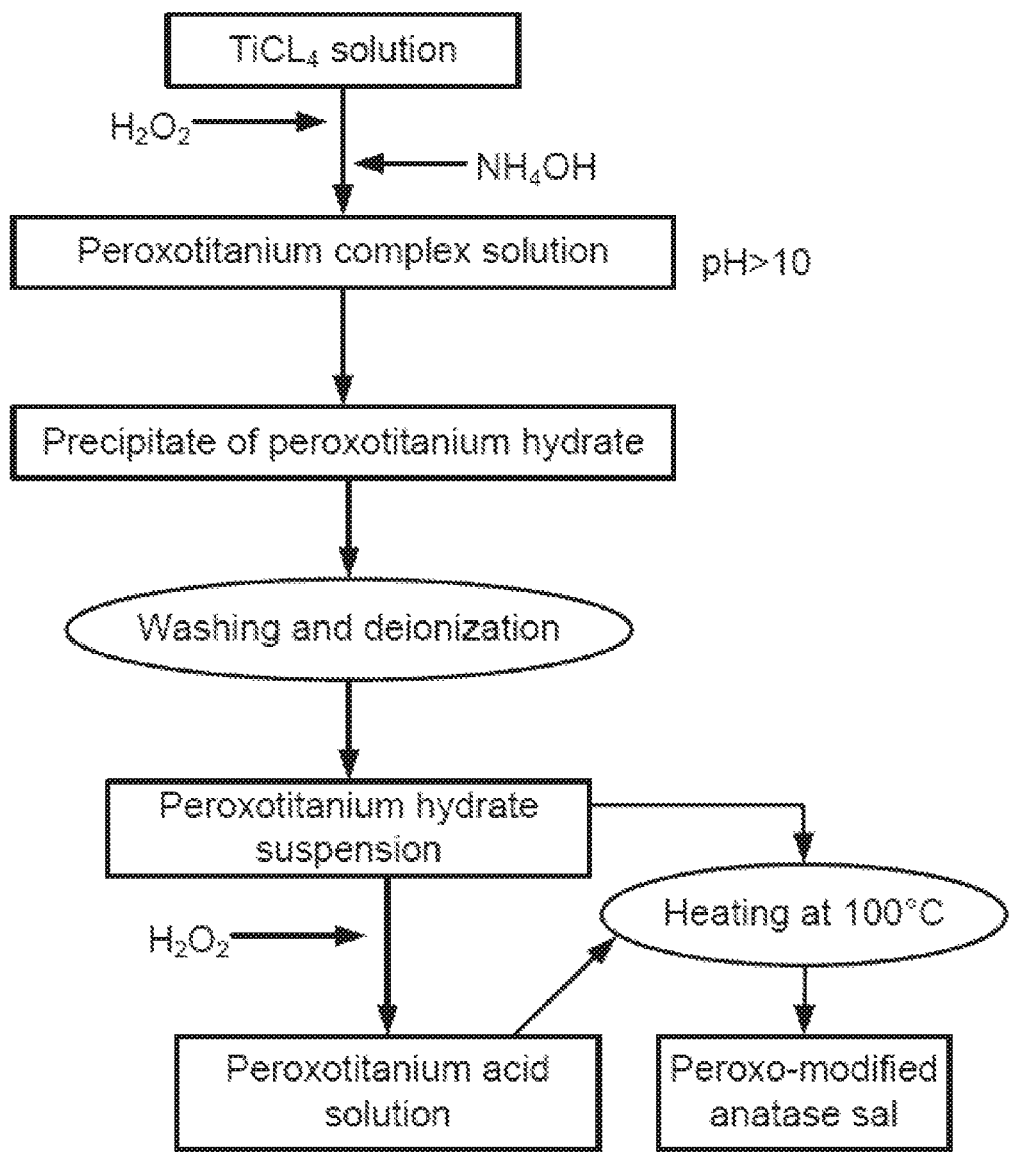
FIG. 4 shows a flowchart of an embodiment of a synthetic procedure to produce peroxotitanium acid solution and peroxo-modified anatase sol, in accordance with various embodiments.

A method to prepare both Peroxotitanium acid solution and Peroxo-modified anatase sol is disclosed in Ichinose, H., et al., *Journal of Sol-Gel Science and Technology*, September 2001, Volume 22, Issue 1-2, pp 33-40. This publication discloses, inter alia, Reaction Scheme 1, shown in FIG. 4, which summarizes the synthetic procedure for both Peroxotitanium acid solution and Peroxo-modified anatase sol. Further disclosure is found in Ichinose, H., et al., *J. Ceramic Soc. Japan*, Volume 104, Issue 8, pp 715-718 (1996).

In various embodiments of Applicants' composition and method, Applicants' coating formulation comprises a mixture of Peroxotitanium acid solution and Peroxo-modified anatase sol. In another embodiment of Applicants' composition and method, a coating is formed on a surface of an object, where that coating comprises a plurality of titanium-oxygen bonds in combination with a plurality of silicon-oxygen bonds, and where that coating is formed by disposing a mixture of Peroxotitanium acid solution and Peroxo-modified anatase sol, in combination with an organosilane onto the surface.

In various embodiments, a coating comprising a plurality of titanium-oxygen bonds in combination with a plurality of silicon-oxygen bonds is formed by first disposing on the surface an organosilane followed by disposing a mixture of Peroxotitanium acid solution and Peroxo-modified anatase sol onto the organosilane.

In various embodiments, a coating comprising a plurality of titanium-oxygen bonds in combination with a plurality of silicon-oxygen bonds is formed by first disposing a mixture of Peroxotitanium acid solution and Peroxo-modified anatase sol on the surface followed by disposing an organosilane onto the mixture of Peroxotitanium acid solution and Peroxo-modified anatase sol. In various embodiments, a coating comprising a plurality of titanium-oxygen bonds in combination with a plurality of silicon-oxygen bonds is formed by simultaneously disposing a mixture of Peroxotitanium acid solution and Peroxo-modified anatase sol and an organosilane onto the surface.

In various embodiments, Applicants' organosilane comprises organosilane 1.

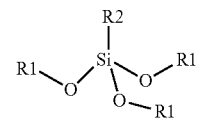

In various embodiments, both R1 and R2 are alkyl. In other embodiments R1 is alkyl and R2 is alkyl with an amino moiety. In various embodiments, R1 is alkyl and R2 comprises a quaternary ammonium group. In various embodiments, R1 is alkyl and R2 comprises a chlorine moiety. In various embodiments, R1 is alkyl and R2 is selected from the group consisting of —O—CH$_3$ and —O—CH$_2$—CH$_3$.

In various embodiments, Applicants' organosilane comprises a trihydroxy silane 2. In various embodiments, R2 is alkyl. In other embodiments R2 is alkyl with an amino moiety. In various embodiments, R2 comprises a quaternary ammonium group. In various embodiments, comprises a chlorine moiety. In various embodiments, R2 is —OH.

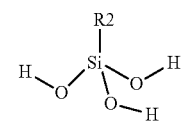

In various embodiments, Applicants' organosilane comprises a silanetriol 2, wherein R2 is alkyl. In other embodiments, Applicants' organosilane comprises a silanetriol 2, wherein R2 is alkyl with an amino moiety. In various embodiments, Applicants' organosilane comprises a silanetriol 2, wherein R2 is alkyl with a quaternary ammonium group.

As those skilled in the art will appreciate and as shown in Equation (1), silyl esters, such as silyl ester 1, are readily hydrolysable into a corresponding silanetriol, such as silanetriol 2. Even exposure to atmospheric moisture is sufficient to hydrolyze silyl ester 1 into silanetriol 2.

EQUATION (1)

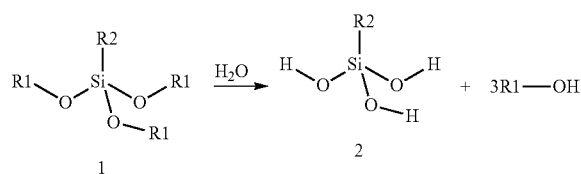

A silsesquioxane is an organosilicon compound 3. In various embodiments, R2 is alkyl. In other embodiments, R2 is alkyl with an amino moiety. In various embodiments, R2 is alkyl with a chlorine moiety. In various embodiments, R2 is alkyl with a quaternary ammonium group.

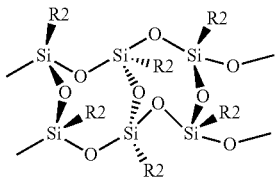

In various embodiments, after application of Applicants' silanetriol 2 to either a hard surface, i.e. wall, door, table, and the like, or a soft surface, i.e. bedding, draperies, furniture cushions, and the like, a resulting coating disposed on the hard surface/soft surface comprises a plurality of silsesquioxane 3 structures. In various embodiments, after application of Applicants' silanetriol 2 in combination with titanium dioxide to either a hard surface, i.e. wall, door, table, and the like, or a soft surface, i.e. bedding, draperies, furniture cushions, and the like, a resulting coating disposed on the hard surface/soft surface comprises a plurality of silsesquioxane structures 3 in combination with Applicants' Titanium-Oxygen Moieties.

In various embodiments, an antimicrobial coating composition herein comprises an aqueous solution of dimethyloctadecyl 3-(trimethoxysilyl)propyl ammonium chloride. In water, this material likely exists as the silanetriol, i.e., 3-(trihydroxysilyl)propyl dimethyloctadecyl ammonium chloride. In various examples, an antimicrobial coating composition is made by diluting dimethyloctadecyl 3-(trimethoxysilyl)propyl ammonium chloride in water. A non-limiting commercial source of dimethyloctadecyl 3-(trimethoxysilyl)propyl ammonium chloride is Sigma-Aldrich, in the form of a 42 wt. % actives solution in methanol. In other examples, an antimicrobial coating composition is made by diluting 3-(trihydroxysilyl)propyl dimethyloctadecyl ammonium chloride in water.

In various embodiments, an antimicrobial coating composition comprises an aqueous mixture of 3-(trihydroxysilyl)propyl dimethyloctadecyl ammonium chloride. 3-(trihydroxysilyl)propyl dimethyloctadecyl ammonium chloride is commercially available from INDUSCO, Inc. in 0.5 wt. %, 0.75 wt. %, 1.5 wt. %, 5.0 wt. % and 71.20 wt. % aqueous solutions, under the trade name BioShield®. The 5 wt. % solution of 3-(trihydroxysilyl)propyl dimethyloctadecyl ammonium chloride is also available from INDUSCO, Inc. under the trade name ProShield® 5000D, having EPA Reg. No. 53053-8. The label for ProShield® 5000D further lists the active ingredient as "octadecylaminodimethyltrihydroxysilyl propyl ammonium chloride," (which is perhaps an incorrect name for 3-(trihydroxysilyl)propyl dimethyloctadecyl ammonium chloride). Another supplier of 5 wt. % aqueous octadecylaminodimethyltrihydroxysilyl propyl ammonium chloride is Gelest, Inc., 11 East Steel Rd., Morrisville, Pa. 19067 USA. The Gelest MSDS discloses this product as containing 94-96 wt. % water and 4-6 wt. % octadecylaminodimethyltrihydroxysilyl propyl ammonium chloride. These various commercial materials may be used "as is" or diluted with water and/or other solvents as necessary to obtain the desired finished weight percent concentration of quaternary silane, e.g. for example, 0.75 wt. %.

In various embodiments, an antimicrobial coating composition comprises an aqueous mixture of dimethyloctadecyl 3-(trimethoxysilyl)propyl ammonium chloride and at least one amine.

In various embodiments, antimicrobial coating compositions comprise at least one amine having structure $R^9R^{10}R^{11}N$, wherein $R^9$, $R^{10}$, and $R^{11}$ are independently H, alkyl, substituted alkyl, aryl, substituted aryl or cyclic. In certain examples, an organic amine comprises diethanolamine or triethanolamine.

In certain aspects, the antimicrobial coating composition comprises a secondary or tertiary amine. In certain examples, an antimicrobial coating composition may comprise dimethyloctadecyl 3-(trimethoxysilyl)propyl ammonium chloride and triethanolamine or diethanolamine. In certain examples, an antimicrobial coating composition comprises an aqueous mixture of from about 0.5 wt. % to about 1.0 wt. % dimethyloctadecyl 3-(trimethoxysilyl)propyl ammonium chloride. In various examples, an antimicrobial coating composition further comprises from about 0.01 wt. % to about 0.10 wt. % triethanolamine.

In various embodiments, an antimicrobial coating composition comprises about 0.75 wt. % dimethyloctadecyl 3-(trimethoxysilyl)propyl ammonium chloride; about 0.045 wt. % triethanolamine; and about 99.205 wt. % water.

In various embodiments, an antimicrobial coating composition comprises an aqueous mixture of 3-(trihydroxysilyl)propyl dimethyloctadecyl ammonium chloride and at least one amine. In certain aspects, the amine may be a secondary or tertiary amine. For example, an antimicrobial coating composition may comprise 3-(trihydroxysilyl)propyl dimethyloctadecyl ammonium chloride and triethanolamine or diethanolamine. In certain examples, an antimicrobial coating composition comprises an aqueous mixture of from about 0.5 wt. % to about 1.0 wt. % 3-(trihydroxysilyl)propyl dimethyloctadecyl ammonium chloride. In various examples, an antimicrobial coating composition comprises from about 0.01 wt. % to about 0.10 wt. % triethanolamine.

In various embodiments, an antimicrobial coating composition comprises about 0.75 wt. % 3-(trihydroxysilyl)propyl dimethyloctadecyl ammonium chloride; about 0.045 wt. % triethanolamine; and about 99.205 wt. % water.

In various embodiments, an antimicrobial coating composition comprises an aqueous mixture of dimethyloctadecyl 3-(trimethoxysilyl)propyl ammonium chloride, at least one amine, and 3-chloropropyltrimethoxysilane and/or 3-chloropropylsilanetriol. Some commercially sourced dimethyloctadecyl 3-(trimethoxysilyl)propyl ammonium chloride or 3-(trihydroxysilyl)propyl dimethyloctadecyl ammonium chloride may contain small amounts of 3-chloropropyltrimethoxysilane. A commercial synthesis of dimethyloctadecyl 3-(trimethoxysilyl)propyl ammonium chloride comprises the $S_N2$ reaction between dimethyloctadecylamine and 3-chloropropyltrimethoxysilane. In some embodiments, an excess of 3-chloropropyltrimethoxysilane may be used to drive this reaction to completion. If not separated out from the reaction product mixture, the unreacted 3-chloropropyltrimethoxysilane may remain in the sample of dimethyloctadecyl 3-(trimethoxysilyl)propyl ammonium chloride. For example, a commercial source of 3-(trihydroxysilyl)propyl dimethyloctadecyl ammonium chloride may be disclosed to comprise 5.0 wt. % 3-(trihydroxysilyl)propyl dimethyloctadecyl ammonium chloride and 1.0 wt. % 3-chloropropyltrimethoxysilane.

In various embodiments, an antimicrobial coating composition comprises 3-chloropropyltrimethoxysilane and dimethyloctadecyl 3-(trimethoxysilyl)propyl ammonium chloride and/or 3-(trihydroxysilyl)propyl dimethyloctadecyl ammonium chloride. In various examples, 3-chloropropyltrimethoxysilane may be added to a solution of dimethyloctadecyl 3-(trimethoxysilyl)propyl ammonium chloride and/or 3-(trihydroxysilyl)propyl dimethyloctadecyl ammonium chloride known to not comprise any 3-chloropropyltrimethoxysilane as a byproduct. In other examples, additional 3-chloropropyltrimethoxysilane may be added to a solution of dimethyloctadecyl 3-(trimethoxysilyl)propyl ammonium chloride and/or 3-(trihydroxysilyl)propyl dimethyloctadecyl ammonium chloride known to include some residual 3-chloropropyltrimethoxysilane as a byproduct.

In various embodiments, an antimicrobial coating composition comprises from about 0.5 wt. % to about 1.0 wt. % dimethyloctadecyl 3-(trimethoxysilyl)propyl ammonium chloride; from about 0.05 to about 0.5 wt. % 3-chloropropyltrimethoxysilane and from about 0.01 wt. % to about 0.10 wt. % triethanolamine, with the remainder being water.

In various embodiments, an antimicrobial coating composition comprises from about 0.5 wt. % to about 1.0 wt. % 3-(trihydroxysilyl)propyl dimethyloctadecyl ammonium chloride; from about 0.05 to about 0.5 wt. % 3-chloropropyltrimethoxysilane and from about 0.01 wt. % to about 0.10 wt. % triethanolamine, with the remainder being water.

In various embodiments, an antimicrobial coating composition comprises about 0.75 wt. % dimethyloctadecyl 3-(trimethoxysilyl)propyl ammonium chloride; about 0.06 wt. % 3-chloropropyltrimethoxysilane; about 0.045 wt. % triethanolamine; and about 99.145 wt. % water. When applied to a portion of a surface and allowed to dry, this composition provides a biostatic coating. In various embodiments, the treated surface comprises a mixture of quaternary and 3-chloropropyl surface bound silanes.

In various embodiments, an antimicrobial coating composition comprises about 0.75 wt. % 3-(trihydroxysilyl)propyl dimethyloctadecyl ammonium chloride; about 0.06 wt. % 3-chloropropyltrimethoxysilane; about 0.045 wt. % triethanolamine; and about 99.145 wt. % water. When applied to a portion of a surface and allowed to dry, this composition provides a biostatic coating. In various embodiments, the treated surface comprises a mixture of quaternary and 3-chloropropyl surface bound silanes.

In various embodiments, an antimicrobial coating composition comprises about 0.75 wt. % dimethyloctadecyl 3-(trimethoxysilyl)propyl ammonium chloride; about 0.12 wt. % 3-chloropropyltrimethoxysilane; about 0.045 wt. % triethanolamine; and about 99.085 wt. % water. When applied to a portion of a surface and allowed to dry, this composition provides a biostatic coating. In various embodiments, the treated surface comprises a mixture of quaternary and 3-chloropropyl surface bound silanes.

In various embodiments, an antimicrobial coating composition comprises about 0.75 wt. % 3-(trihydroxysilyl)propyl dimethyloctadecyl ammonium chloride; about 0.12 wt. % 3-chloropropyltrimethoxysilane; about 0.045 wt. % triethanolamine; and about 99.085 wt. % water. When applied to a portion of a surface and allowed to dry, this composition provides a biostatic coating. In various embodiments, the treated surface comprises a mixture of quaternary and 3-chloropropyl surface bound silanes.

In various embodiments, an antimicrobial coating composition comprises about 0.75 wt. % dimethyloctadecyl 3-(trimethoxysilyl)propyl ammonium chloride; about 0.26 wt. % 3-chloropropyltrimethoxysilane; about 0.045 wt. % triethanolamine; and about 98.945 wt. % water. When applied to a portion of a surface and allowed to dry, this composition provides a biostatic coating. In various embodiments, the treated surface comprises a mixture of quaternary and 3-chloropropyl surface bound silanes.

In various embodiments, an antimicrobial coating composition comprises about 0.75 wt. % 3-(trihydroxysilyl)propyl dimethyloctadecyl ammonium chloride; about 0.26 wt. % 3-chloropropyltrimethoxysilane; about 0.045 wt. % triethanolamine; and about 98.945 wt. % water. When applied to a portion of a surface and allowed to dry, this composition provides a biostatic coating. In various embodiments, the treated surface comprises a mixture of quaternary and 3-chloropropyl surface bound silanes.

In various embodiments, a surface is treated with an antimicrobial coating composition comprising: about 0.75 wt. % 3-(trihydroxysilyl)propyl dimethyloctadecyl ammonium chloride; about 0.045 wt. % triethanolamine; and about 99.205 wt. % water, and allowed to visibly dry. In one non-limiting example, borosilicate glass slides were positioned vertically and electrostatic spray coated from a distance of about 5 to 6 feet with this composition. The treated slides were allowed to dry at room temperature overnight. AFM imaging (49 μm×74 μm scan area) revealed the silane/triethanolamine coating to have an average thickness of 22.12±3.28 nm, and an average roughness of 19.85±5.62 nm.

As used herein, the term "titanium (IV) species" refers to any chemical compound comprising at least one tetravalent titanium atom, regardless if monomeric, dimeric, trimeric, or polymeric. Non-limiting examples include titanium (IV) oxide ($TiO_2$) in any form, other Ti(IV) species, (e.g., $TiCl_4$, Ti—(O-i-$C_3H_7$)$_4$ or any other Ti(IV) alkoxide, phenoxide or halide). Various forms of $TiO_2$ for use herein include, but are not limited to, rutile, anatase, brookite, hollandite-like, ramsdellite-like, α-$PbO_2$-like, baddeleyite-like form, orthorhombic $TiO_2$—OI, cubic, and/or cotunnite-like forms. The most common crystalline forms are anatase, brookite and rutile. In various examples, Ti(IV) species for use herein comprise Ti nanoparticles. Further, Ti(IV) species for use herein include "titanyl-oxide moieties," which is a broad term defined herein to include any and all Ti compounds and mixtures known to form $TiO_2$ thin films, or at least suspected as able to form $TiO_2$ thin films, such as via the sol-gel process. A titanyl sol-gel is a precursor in the preparation of $TiO_2$ thin films. For example, a mixture of Ti($OC_4H_9$)$_4$, ethanol, water, and diethanolamine, in a 1:26.5:1:1 molar ratio, has been disclosed as forming a $TiO_2$ film (see J. Yu, et al., *Materials Chemistry and Physics*, vol. 69, pp 25-29 (2001)). This reference further discloses that whether or not the film is photocatalytic depends, inter alia, on the curing conditions for the sol-gel after surface application, e.g. using high temperatures. In another non-limiting example, a sol-gel route to mesoporous and nanocrystalline anatase thin layers begins with acidic hydrolysis of titanium isopropoxide, (see F. Bosc, *Chem. Mater.*, 15(12), pp 2463-2468, (2003)).

In certain examples, titanyl-oxide moieties for use herein comprise a colloidal suspension of from about 0.5 wt. % to about 50 wt. % $TiO_2$ in water. In other examples, titanyl-oxide moieties comprise an aqueous mixture of Ti—(O-i-$C_3H_7$)$_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—(O-i-$C_3H_7$)$_4$ or $TiCl_4$. A TiO$_2$ sol-gel composition, when coated onto a portion of a surface, provides a thin film TiO$_2$ coating on the portion of the surface.

In various embodiments, titanyl-oxide moieties comprise Ti(OR$^3$)$_4$, wherein R$^3$ is alkyl, substituted alkyl, aryl, or substituted aryl, and wherein the four separate R$^3$ groups are identical or different. Examples of Ti(OR$^3$)$_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-C$_3$H$_7$)$_4$) or dissolved in an alcohol or other organic solvent(s), such as the corresponding alcohol, where feasible, (methanol, ethanol, i-propanol, etc.). Thus, titanyl-oxide moieties may in some instances comprise a solution of Ti—(O-i-C$_3$H$_7$)$_4$ in isopropanol or some other alcohol.

In various embodiments, titanyl-oxide moieties comprise Ti(OR$^3$)$_4$, wherein R$^3$ is alkyl, substituted alkyl, aryl, or substituted aryl. In certain aspects, titanyl-oxide moieties may further comprise a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, titanyl-oxide moieties consist essentially of Ti—(O-i-C$_3$H$_7$)$_4$. Other examples include Ti—(O-i-C$_3$H$_7$)$_4$ and an alcohol, and a composition comprising Ti—(O-i-C$_3$H$_7$)$_4$ and isopropanol.

In various examples, titanyl-oxide moieties for use herein comprise an aqueous solution of peroxotitanium acid and peroxo-modified anatase sol, which is disclosed in the literature as a room temperature route to TiO$_2$ thin films, (see Ichinose, H., et al., *Journal of Sol-Gel Science and Technology*, September 2001, Volume 22, Issue 1-2, pp 33-40, and Ichinose, H., et al., *J. Ceramic Soc. Japan*, Volume 104, Issue 8, pp 715-718 (1996)).

In various examples, the titanyl-oxide moieties for use herein is a sol-gel that comprises about 0.5 wt. % peroxotitanium acid and about 0.5 wt. % peroxo-modified anatase sol, remainder water. A non-limiting example of a titanyl-oxide moieties composition for use herein comprises 0.85 wt. % of a mixture of peroxotitanium acid and peroxo-modified anatase sol (titanium oxide (IV)), remainder water. In various examples, a titanyl-oxides moieties composition comprises 0.8-0.9 wt. % of a mixture of titanium oxide (IV) and peroxotitanium acid, with the remainder, i.e., 99.1-99.2 wt. %, water. In various embodiments, this sol-gel mixture may be referred to as "0.85 wt. % aqueous peroxotitanium acid and peroxo-modified anatase sol."

This titanyl sol-gel, or others prepared by other processes as discussed, may be coated onto a surface by itself, or in combination with an antimicrobial silane coating. In an example where the surface comprised a borosilicate glass slide, AFM imaging (50 μm$^2$ scan area) revealed a 0.85 wt. % aqueous peroxotitanium acid and peroxo-modified anatase sol coating, when dry, to have an average roughness of 25.76 nm. In an example where the surface comprised mica, AFM imaging (1 μm$^2$ scan area) revealed a 0.85 wt. % aqueous peroxotitanium acid and peroxo-modified anatase sol coating, when dry, provides an average particle size of 30 nm. Although not wishing to be bound by any particular theory, these particles may comprise, at least in part, nanoparticulate TiO$_2$.

In various embodiments, an antimicrobial coating is prepared on a portion of a surface by a method comprising: (1) coating the portion of the surface with an aqueous mixture comprising 3-(trihydroxysilyl)propyl dimethyloctadecyl ammonium chloride; triethanolamine; and water; and (2) coating the same portion of the surface with aqueous peroxotitanium acid and peroxo-modified anatase sol, in either order (i.e., (1) then (2), or (2) then (1)). Not wishing to be bound by any particular theory, the peroxotitanium acid and peroxo-modified anatase sol coating may assist in adhering the 3-(trihydroxysilyl)propyl dimethyloctadecyl ammonium chloride to the portion of the surface, and/or may increase the hydrophilicity of the portion of the surface previously made hydrophobic by surface bound 3-(trihydroxysilyl) propyl dimethyloctadecyl ammonium chloride. Either of these phenomena are possible regardless of the order of disposition on the portion of the surface.

In various embodiments, an antimicrobial coating is prepared on a surface by a method comprising: (1) coating a portion of the surface with an aqueous mixture comprising: 0.75 wt. % 3-(trihydroxysilyl)propyl dimethyloctadecyl ammonium chloride; 0.045 wt. % triethanolamine; and 99.205 wt. % water; and (2) subsequently coating the portion of the surface with 0.85 wt. % aqueous peroxotitanium acid and peroxo-modified anatase sol. In a non-limiting example, borosilicate glass slides were positioned vertically and electrostatic spray coated from a distance of about 5 to 6 feet with the aqueous 3-(trihydroxysilyl)propyl dimethyloctadecyl ammonium chloride and triethanolamine solution and allowed to dry about 3 to 5 minutes, after which time the 0.85 wt. % aqueous peroxotitanium acid and peroxo-modified anatase sol was electrostatic spray coated overtop of the organosilane from about 5 to 6 feet distance. The treated slides were left to dry at room temperature overnight. AFM imaging (50 μm$^2$ scan area) revealed that the coating resulting from this two-step sequential surface treatment had an average thickness of 51.79±17.98 nm, and an average roughness of 35.90±9.43 nm.

The method of stepwise surface treatment may be performed in the opposite order. For example, a portion of a surface may be coated first with an aqueous solution of peroxotitanium acid and peroxo-modified anatase sol, and then the same portion of the surface subsequently coated with an aqueous solution of 3-(trihydroxysilyl)propyl dimethyloctadecyl ammonium chloride and triethanolamine such that the organosilane is theoretically overtop the titanyl species. For either order of application, the first coating may be allowed to partly dry or completely dry prior to the subsequent coating. In other aspects, the first treatment may be applied, and while still wet, followed by the second treatment, and then the combined treatments are allowed to dry. Throughout this disclosure, stepwise treatment of a surface is meant to target approximately the same portion of the surface with successive compositions. In some instances, a second treatment may liquefy a coating applied first and dissolve those components that were first dried on the surface.

The following Examples are presented to further illustrate to persons skilled in the art how to make and use certain aspects of the present disclosure. These Examples are not intended as limitations, however, upon the scope of the disclosure.

Example I

A study was conducted at the Glendale Memorial Hospital and Health Center in Glendale, Calif. (the "Glendale Memorial Hospital Study"). The Center has a 24 bed intensive care (ICU). The study was performed between May 10 and Sep. 30, 2013.

The Glendale Memorial Hospital Study was designed to assess the anti-microbial properties of Applicants' coating composition and method, wherein the method employed utilized an initial coating of Applicants' organosilane followed by an overspray of titanium dioxide. The entire ICU was subjected to the two step spray regime to treat all objects in each room including hard surfaces (beds, tray tables, bed rail, walls, etc.) and soft surfaces (drapes, cloth and vinyl covered chairs, woven fabrics, non-woven fabrics, leather goods, and the like). The goal of the Glendale Memorial Hospital Study was to assess the anti-microbial efficacy of Applicants' coating composition in a practical application in a health care environment.

Each surface was first electrostatically spray coated at room temperature using an aqueous composition formed by mixing Octadecylaminodimethyltrihydroxysilylpropyl Ammonium Chloride 6 at 3.6 weight percent in water.

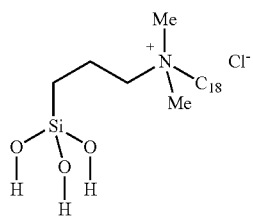

6

About fifteen (15) minutes after the electrostatic spray coating using the aqueous mixture of Octadecylaminodimethyltrihydroxysilylpropyl Ammonium Chloride 6, most of the water had evaporated leaving a coating comprising at least ninety weight percent (90 wt. %) Octadecylaminodimethyltrihydroxysilylpropyl Ammonium Chloride 6. Thereafter, each surface was then electrostatically spray coated at room temperature using Applicants' Titanium-Oxide Moieties. After about 15 minutes, most of the water in the second spray deposition had evaporated leaving a coating comprising at least ninety weight percent (90 wt. %) Applicants' Titanium-Oxide Moieties.

The treated surfaces were maintained at room temperature during the spray deposition of the aqueous Octadecylaminodimethyltrihydroxysilylpropyl Ammonium Chloride 6, and during the spray deposition of Applicants' Titanium-Oxide Moieties. None of the treated objects were subjected to any elevated heat treatment wherein the treated surface was heated to a temperature greater than about room temperature during or after completion of Applicants' spray coating regime.

Applicants have found that using their two step, spray coating protocol described hereinabove, after evaporation of the water from the spray deposited Titanium-Oxide Moieties and evaporation of the water portion from the spray deposited aqueous Octadecylaninodimethyltrihydroxysilylpropyl Ammonium Chloride, the combined weight of Applicants' Titanium-Oxide Moieties and Octadecylaminodimethyltrihydroxysilylpropyl Ammonium Chloride disposed on a treated surface was measured as 0.76 mg/in$^2$.

Initial microbial sampling of various fomites was conducted to assess the levels of bacteria on various hospital surfaces before selecting study sites. After review, 95 sites were selected for the study in the ICU. Each of the ninety-five (95) specific sites in the ICU were selected for recurring sampling at weeks 1, 2, 4, 8, and 15, after application of Applicants' composition. Those selected sites included bed rails, bed controls, tray tables, and walls above sinks. Samples were also collected from the two ICU nursing stations and waiting lobby including countertops, phones, computer keyboards, chair armrests and end tables. All movable items were inconspicuously tagged and coded over the course of the study so that the same objects could be sampled.

Each of the sites was cultured prior to application of Applicants' method and at 1 week (6-8 days), 2 weeks (13-17 days), 4 weeks (29-32 days), 8 weeks (59-62 days), 15 weeks (104-107 days) after application. Some objects were removed and were not available for culture at some of the subsequent time points.

Areas of 100 cm$^2$ were sampled using a sponge stick containing Letheen broth (3M, St. Paul, Minn.) to neutralize any residual disinfectant. After collection the samples were immediately placed on ice packs and sent overnight to the University of Arizona. Upon receipt the broth was extracted from the sponge stick by manual agitation, and then 4 mL of extracted broth was assayed using selective media for isolation of the various bacteria. Samples were cultured for total bacteria, *Clostridium difficile*, methicillin-resistant *Staphylococcus aureus* (MRSA), vancomycin-resistant *Enterococcus* (VRE), and carbapenem-resistant Enterobacteriaceae (CRE). Test methods for each organism are presented in the table in FIG. 5.

The average number of total bacteria detected per 100 cm$^2$ at all locations and percent reductions in total bacterial numbers after treatment are shown in FIG. 6.

As can be seen bacterial numbers were always 99.9% less after the treatment for four weeks, 99% after eight weeks and still almost 99% after 15 weeks.

Also, significantly the number of sites containing more than 10,000 CFU/100 cm$^2$ was reduced from 25.2% of the sites before treatment to zero for the next eight weeks and after even 15 weeks only 11.1% of the sites exceeded this number as shown in the table in FIG. 7.

Bootstrapping Analysis of Variance (ANOVA) was conducted for each stage between the baseline concentrations for the sampled fomites and the intervention concentrations for the same fomites to determine statistical significant differences based on a rejection region of 5%. Based on the p-values (<0.0005) there was a statistical significance difference between the baseline concentrations and the fomite concentrations during the entire 15 weeks of the study.

The percent of samples in which antibiotic resistant bacteria were isolated at the different sites sampled is shown in the table in FIG. 8.

Antibiotic resistant bacteria were isolated from all study areas during the baseline sampling, except *C. difficile*. VRE was the most commonly isolated organism.

Prior to treatment antibiotic resistant bacteria were isolated from 25% of the sites sampled. After treatment, no antibiotic bacteria were isolated until week 8, when VRE in 1 sample (from a chair armrest) of 64 samples (1.5%) was found.

The present study demonstrates that the use of Applicants' method reduced the numbers of bacteria on fomites by greater than 99% for 8 weeks after a single treatment (FIG. 6).

Levels of bacteria were reduced by 99.9% at 4 weeks post-treatment. Overall average levels of bacteria never returned to those observed before treatment. Bacterial numbers increased between 8 and 15 weeks post-treatment but the average bacterial count on all treated surfaces was still less than 90% after 15 weeks. No values above 10,000 CFU/100 cm$^2$ were seen for 4 weeks after treatment vs. 25.2% pre-treatment and even after 15 weeks only 11.1% of the values exceeded this amount.

No antibiotic resistant bacteria were isolated until 8 weeks after the treatment, and then at levels below that seen before the treatment (FIG. 8). No MRSA or CRE were isolated even after 15 weeks post-treatment and VRE only after 8 weeks. No C. difficile were isolated during the baseline or after the treatment. However, C. difficile was isolated in the initial screening used to select the sampling sites.

In conclusion, the anti-microbial effects resulting from use of Applicants' composition and method was found to have persisted over 15 weeks in reducing the total number of bacteria and antibiotic resistant bacteria on both hard surfaces and soft surfaces within an ICU. The hard surfaces included bare metal surfaces, painted metal surfaces, epoxy-coated surfaces, unpainted wood surfaces, painted wood surfaces, and glass.

The fifteen weeks antimicrobial efficacy demonstrates that Applicants' composition forms a coating on a treated surface, where that coating is both antifouling and antimicrobial. Applicants' composition and the resulting coating formed therefrom can generate self-decontaminating surfaces that comprise both antifouling and antimicrobial properties, thereby, providing a cost-effective route to minimize transmission of disease via high touch surfaces in healthcare and industrial applications.

FIG. 1 graphically shows the number of hospital acquired C-difficile infections in the Glendale Memorial Hospital ICU from January 2012 through February 2014. FIG. 1 indicates that with the exception of September 2013, there were no hospital acquired C-difficile infections originating in the ICU during the period May 2013 through November 2013. Thus, FIG. 1 shows that there was a single hospital acquired C-difficile infection originating in the ICU during the six month period May 2013 through November 2013.

FIG. 1 further shows that, other than the six month period May 2013 through November 2013, there was no other 6 month period during the 25 months from January 2012 through February 2014 wherein only a single hospital acquired C-difficile infection originated in the ICU. All surfaces in the ICU were treated as described hereinabove during the first week of May 2013 as part of the Glendale Memorial Hospital Study.

Figure 2:
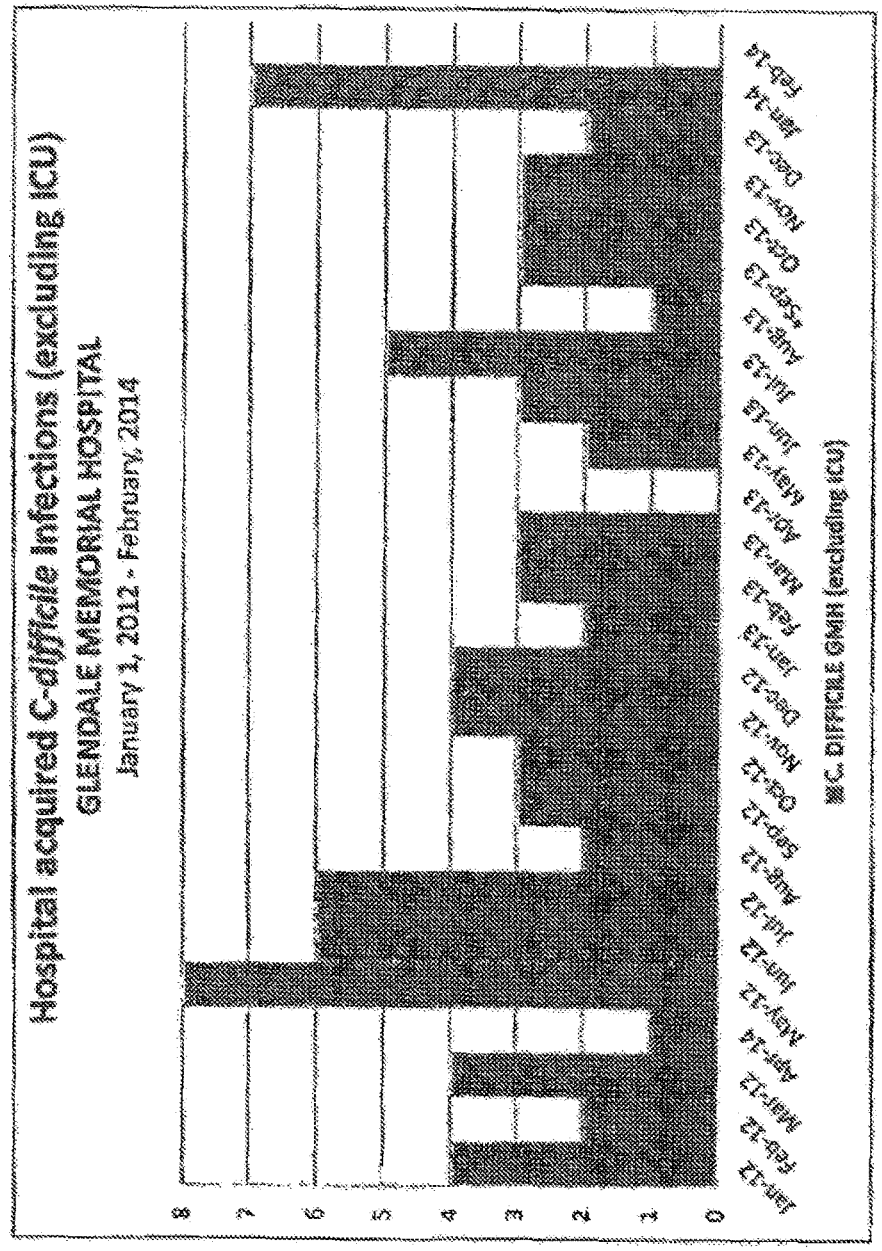
FIG. 2 graphically shows the number of hospital acquired C-difficile infections at the Glendale Memorial Hospital (excluding ICU) from January 2012 through February 2014, in accordance with various embodiments.

FIG. 2 graphically shows the number of hospital acquired C-difficile infections at the Glendale Memorial Hospital (excluding ICU) from January 2012 through February 2014. FIG. 2 indicates that, with the exception of April 2013, there were between 1 and 8 hospital acquired C-difficile infections every month during the 25 month period in hospital areas outside of the ICU. During the period May 2013 through November 2013, FIG. 2 shows that there were a total of 20 hospital acquired C-difficile infections originating outside of the ICU at the Glendale Memorial Hospital.

FIGS. 1 and 2 show that during the period May 2013 through November 2013, a single hospital acquired C-difficile infection originated in the ICU at the Glendale Memorial Hospital, and a total of 20 hospital acquired C-difficile infections originated outside of the ICU at the Glendale Memorial Hospital.

Applicants have found that they can dispose Octadecylaminodimethyltrihydroxysilylpropyl Ammonium Chloride and Applicants Titanium-Oxide Moieties, by spray deposition or by dip coating, onto a dressing prior to use of that dressing to cover a wound. As those skilled in the art will appreciate, a dressing is a sterile pad or compress applied to a wound to promote healing and/or prevent further harm. A dressing is designed to be in direct contact with the wound, as distinguished from a bandage, which is most often used to hold a dressing in place. In various embodiments, Applicants' wound dressings including the following: alginates and other fiber gelling dressings including ropes and sheets, composite dressings, foam dressings with and without adhesive border, gauze with and without adhesive border, hydrocolloids, specialty absorptive dressings with and without adhesive borders, transparent films, collagen dressings sheets and ropes, hydrogel sheets with and without adhesive border, cotton packing strips, roll gauze, paper tape, silk tape, compression bandages (elastic, knitted/woven), self-adherent bandage (elastic, non-knitted/non-woven).

Example II

This Example II disposes the components of Applicants' composition onto a target surface in a reverse order. More specifically in this Example II, Applicants' first dispose Applicants' Titanium-Oxide Moieties onto the target surface, the aqueous portion of the first spray deposition is evaporated, and then dispose Octadecylaminodimethyltrihydroxysilylpropyl Ammonium Chloride 6 over the earlier-disposed Titanium-Oxide Moieties.

The test coupons of this Example II were prepared and using the Procedure recited immediately hereinbelow. In various embodiments, the treated coupons were stored for at least four (4) weeks prior to inoculation with various organisms.

FIG. 9 recites efficacy data for the treated coupons after inoculation with E. coli. FIG. 10 recites efficacy data for the treated coupons after inoculation with MS-2. FIG. 11 recites efficacy data for the treated coupons after inoculation with MRSA.

In summary, the tabular data set forth in FIGS. 9, 10 and 11 demonstrate that first disposing Applicants' Titanium-Oxide Moieties onto a target surface followed by disposing Octadecylaminodimethyltrihydroxysilylpropyl Ammonium Chloride 6 over the earlier-formed Titanium-Oxide Moieties coating, generates a self-decontaminating surface.

Procedure

Put on sterile gloves.
Prepare the test coupons by wiping them first with ISP Alcohol and allowing to dry.
Clean the test coupons with surface cleaner using a microfiber cloth.
Hold sprayer about eight (8) inches from surface to be cleaned.
Spray on let stand for 1-3 minutes and wipe it off, if the area is extremely dirty allow cleaner to stand longer, or apply a second spray and wipe.
Wipe surface with a clean, damp sponge or cloth.
Allow surface to completely dry.
With gloved hands examine coupons for consistency.

First Coat—Applicants' Titanium-Oxide Moieties Application

Add Applicants' Titanium-Oxide Moieties to the applicator container.
Fasten the Liquid Hose/Bottle cap assembly tightly on the container.
Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Rinse spray gun with distilled water prior to applying Applicants' Titanium-Oxide Moieties (unless using 2 sprayers, one for each product).

Second Coat—Organosilane Application

Add the Octadecylaminodimethyltrihydroxysilylpropyl Ammonium Chloride 6 to applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example III

This Example III simultaneously disposes a mixture of Applicants' organosilane and Applicants' Titanium-Oxide Moieties onto the surface of a plurality of test coupons. More specifically in this Example III, Applicants' simultaneously dispose Applicants' Titanium-Oxide Moieties and Octadecylaminodimethyltrihydroxysilylpropyl Ammonium Chloride 6 onto a surface of each test coupon.

The test coupons of this Example III were prepared and using the Procedure recited immediately hereinbelow. In various embodiments, the treated coupons were stored for at least four (4) weeks prior to inoculation with various organisms.

FIG. 12 recites efficacy data for the treated coupons after inoculation with *E. coli*. FIG. 13 recites efficacy data for the treated coupons after inoculation with MS-2. FIG. 14 recites efficacy data for the treated coupons after inoculation with MRSA.

In summary, the tabular data set forth in FIGS. 12, 13 and 14 demonstrate that simultaneously disposing Applicants' Titanium-Oxygen Moieties and Applicants' organosilane onto a target surface generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare Combined Solution

In a measured container combine 50% Octadecylamino dimethyltrihydroxy silyl propyl Ammonium Chloride aqueous mixture and 50% Applicants' Titanium-Oxide Moieties aqueous mixture.

Mix thoroughly.

Coating

Add the aqueous mixture Octadecylaminodimethyltrihydroxysilylpropyl Ammonium Chloride and Applicants' Titanium-Oxide Moieties to applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example IV

This Example IV utilizes (3-Aminopropyl)trimethoxysilane in water as the only organosilane. This being the case, this example does not utilize any organosilane comprising a quaternary ammonium moiety. (3-Aminopropyl)trimethoxysilane is rapidly hydrolyzed to (3-Aminopropyl)trihydroxysilane) 7 when mixed with water.

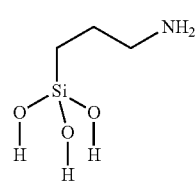

The test coupons of this Example IV were prepared and using the Procedure recited immediately hereinbelow. In various embodiments, the treated coupons were stored for at least four (4) weeks prior to inoculation with various organisms.

Applicants have found that using their two step, spray coating protocol described hereinbelow, after evaporation of the water from the spray deposited Titanium-Oxide Moieties and evaporation of the water portion from the spray deposited aqueous (3-Aminopropyl)trihydroxysilane), the combined weight of Applicants' Titanium-Oxide Moieties and (3-Aminopropyl)trihydroxysilane) disposed on a treated surface was measured as 1.22 mg/in$^2$.

Applicants have found that they can dispose (3-Aminopropyl)trihydroxysilane and Applicants Titanium-Oxide Moieties, by spray deposition or by dip coating, onto a dressing prior to use of that dressing to cover a wound. As those skilled in the art will appreciate, a dressing is a sterile pad or compress applied to a wound to promote healing and/or prevent further harm. A dressing is designed to be in direct contact with the wound, as distinguished from a bandage, which is most often used to hold a dressing in place. In various embodiments, Applicants' wound dressings including the following: alginates and other fiber gelling dressings including ropes and sheets, composite dressings, foam dressings with and without adhesive border, gauze with and without adhesive border, hydrocolloids, specialty absorptive dressings with and without adhesive borders, transparent films, collagen dressings sheets and ropes, hydrogel sheets with and without adhesive border, cotton packing strips, roll gauze, paper tape, silk tape, compression bandages (elastic, knitted/woven), self-adherent bandage (elastic, non-knitted/non-woven).

TABLES 15, 16, and 17, set forth in FIGS. 15, 16 and 17, respectively, recite efficacy data for the treated coupons after inoculation with *E. coli*. In summary, TABLES 15, 16, and 17, demonstrate that disposing a 3-Aminopropyl)trihydroxysilane coating onto a target surface, and then disposing TiO$_2$ over that 3-Aminopropyl)trihydroxysilane coating generates a self-decontaminating surface.

Procedure

Put on sterile gloves.

Prepare the test coupons by wiping them first with ISP Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare Dilution for (3-Aminopropyl)triethoxysilane

Prepare a 10% solution of 3-Aminopropyl)triethoxysilane in Methanol (MeOH) (10 ml silane in 100 ml MeOH).

Prepare Triethanolamine as a 10% solution in MeOH.

Combine the triethanolamine solution and 3-Aminopropyl)triethoxysilane solution in a 1:1 ratio on a stir plate at room temperature (ie—100 ml triethanolamine solution added to 100 ml 3-Aminopropyl)triethoxysilane solution.

First Coat—(3-Aminopropyl)triethoxysilane Application

Add the mixture of triethanolamine and (3-aminopropyl) triethoxysilane to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Rinse spray gun with distilled water prior to applying Applicants' Titanium Oxide Moieties (unless using 2 sprayers, one for each product).

Second Coat—Applicants' Titanium Oxide Moieties Application

Add Applicants' Titanium Oxide Moieties to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow surface to completely dry.

Clean the spray gun with distilled water per manufactures' specifications after each day of use.

Example V

This Example V mixes (3-Chloropropyl)trimethoxysilane in water. (3-Chloropropyl)trimethoxysilane is immediately hydrolyzed to (3-Chloropropyl)trihydroxysilane 8 when mixed with water.

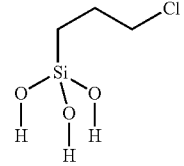

This being the case, this Example V utilizes NO organosilane(s) comprising a quaternary ammonium moiety. Furthermore, this Example VII utilizes NO organosilane(s) comprising an amino moiety.

The test coupons of this Example V were prepared using the Procedure recited immediately hereinbelow. In various embodiments, the treated coupons were stored for at least four (4) weeks prior to inoculation with various organisms.

Applicants have found that they can dispose (3-Chloropropyl)trihydroxysilane and Applicants Titanium-Oxide Moieties, by spray deposition or by dip coating, onto a dressing prior to use of that dressing to cover a wound. As those skilled in the art will appreciate, a dressing is a sterile pad or compress applied to a wound to promote healing and/or prevent further harm. A dressing is designed to be in direct contact with the wound, as distinguished from a bandage, which is most often used to hold a dressing in place. In various embodiments, Applicants' wound dressings including the following: alginates and other fiber gelling dressings including ropes and sheets, composite dressings, foam dressings with and without adhesive border, gauze with and without adhesive border, hydrocolloids, specialty absorptive dressings with and without adhesive borders, transparent films, collagen dressings sheets and ropes, hydrogel sheets with and without adhesive border, cotton packing strips, roll gauze, paper tape, silk tape, compression bandages (elastic, knitted/woven), self-adherent bandage (elastic, non-knitted/non-woven).

TABLES 18, 19, and 20, set forth in FIGS. 18, 19 and 20, respectively, recite efficacy data for the treated coupons after inoculation with *E. coli*. In summary, TABLES 18, 19, and 20, demonstrates that disposing a (3-Chloropropyl)trihydroxysilane coating on a target surface followed by disposing Applicants' Titanium Oxide Moieties onto the (3-Chloropropyl)trihydroxysilane coating generates a self-decontaminating surface.

Procedure

Put on sterile gloves.
Prepare the test coupons by wiping them first with ISP Alcohol and allowing to dry.
Clean the test coupons with surface cleaner using a microfiber cloth.
Hold sprayer about eight (8) inches from surface to be cleaned.
Spray on let stand for 1-3 minutes and wipe it off, if the area is extremely dirty allow cleaner to stand longer, or apply a second spray and wipe.
Wipe surface with a clean, damp sponge or cloth.
Allow surface to completely dry.
With gloved hands examine coupons for consistency.

Prepare Organosilane Dilution for (3-Chloropropyl)trimethoxy silane

Prepare a 10% solution of (3-Chloropropyl)trimethoxy silane in Methanol (MeOH) (10 ml. silane in 100 ml. MeOH).
Prepare Triethanolamine solution as a 10% solution in MeOH.
Combine the triethanolamine solution and (3-Chloropropyl)trimethoxy silane solution in a 1:1 ratio on a stir plate at room temperature (ie—100 ml. trethanolamine added to 100 ml. (3-Chloropropyl)trimethoxy silane).

First Coat—(3-Chloropropyl)trimethoxy silane application

Add the mixture of triethanolamine and (3-chloropropyl) trimethoxy silane to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.

Optimal spraying distance is at least 36 to 48 inches away from the target surface.
Hold the spray gun at right angles to the target surface and spray.
Target surface should just barely glisten with the spray. Do not over-saturate the surface.
Rinse spray gun with distilled water prior to applying Applicants' Titanium Oxide Moieties (unless using 2 sprayers, one for each product).

Second Coat—Applicants' Titanium Oxide Moieties Application

Add Applicants' Titanium Oxide Moieties to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.
Optimal spraying distance is at least 36 to 48 inches away from the target surface.
Hold the spray gun at right angles to the target surface and spray.
Target surface should just barely glisten with the spray. Do not over-saturate the surface.
Allow surface to completely dry.
Clean the spray gun with distilled water per manufactures' specifications after each day of use.

Example VI

This Example VI utilizes three (3) coating formulations without any Titanium-Oxide containing compounds. A first of the three coating formulations identified in this Example VI as ABS 2015E utilizes Octadecylaminodimethyltrihydroxysilylpropyl Ammonium Chloride 6 as the organosilane. A second of the three coating formulations identified in this Example VI as ABS 2020E utilizes (3-Aminopropyl) trihydroxysilane) 7 as the organosilane. A third of the three coating formulations identified in this Example VI as ABS 2030E utilizes (3-Chloropropyl)trihydroxysilane) 8 as the organosilane.

The method of Example IV as discussed above relating to spray deposition of a silane onto test coupons was utilized in this Example VI. The method in Example IV relating to spray deposition of the Titanium-Oxygen Moieties was not utilized in this Example VI.

Table 21 in FIG. 21 recites CFU/mL data for each of the three coating formulations, wherein each formulation did not include one or more titanium-oxide moieties. Table 22 FIG. 22 recites Log Reduction data for the three formulations evaluated, wherein each formulation did not include one or more titanium-oxide moieties. Table 23 in FIG. 23 recites Percent Reduction data for the three formulations utilized, wherein each formulation did not include one or more titanium-oxide moieties.

Example VII

Example VII evaluates the anti-microbial efficacy of coatings prepared from ABS-G2015 (Octadecylaminodimethyltrihydroxysilylpropyl Ammonium Chloride 6 and triethanolamine) followed by Applicants' Titanium Oxide Moieties; ABS-G2020 ((3-chloropropyl)trihydroxysilane 8 and triethanolamine) followed by Applicants' Titanium Oxide Moieties; and ABS G-2030 ((3-aminopropyl)trihydroxysilane 7 and triethanolamine) followed by Applicants' Titanium Oxide Moieties, against Murine Noro Virus. Murine norovirus (MNV) is a species of norovirus affecting mice. Norovirus is the most common cause of viral gastroenteritis in humans. It affects people of all ages. The virus is transmitted by, inter alia, aerosolization of the virus and subsequent contamination of surfaces. The virus affects around 267 million people and causes over 200,000 deaths each year; these deaths are usually in less developed countries and in the very young, elderly and immunosuppressed.

The test coupons for example VII, (stainless steel and Formica as indicated in the data tables) were prepared using the Procedure recited immediately hereinbelow.

Procedure

Put on sterile gloves.

Prepare the test coupons by wiping them first with Isopropyl Alcohol and allowing to dry.

Clean the test coupons with surface cleaner using a microfiber cloth.

Hold sprayer about eight (8) inches from surface to be cleaned.

Spray on let stand for 1-3 minutes and wipe it off, if the area is extremely dirty allow cleaner to stand longer, or apply a second spray and wipe.

Wipe surface with a clean, damp sponge or cloth.

Allow surface to completely dry.

With gloved hands examine coupons for consistency.

Prepare a 10 volume percent solution of the selected silane in Methanol (MeOH) (10 ml silane in 90 ml MeOH).

Prepare Triethanolamine as a 10 volume percent solution in MeOH.

Combine the triethanolamine solution and the silane solution in a 1:1 ratio on a stir plate at room temperature (i.e., 100 ml triethanolamine solution added to 100 ml silane solution).

Silane Application

Add the silane/triethanolamine solution to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow target surface to dry, i.e. allow at least 90 weight percent of the methanol liquid carrier to evaporate to give a deposition consisting essentially of the selected silane and triethanolamine. The deposition onto the target surface consists of at least 33 volume percent of the selected silane, at least 33 volume percent of triethanolamine, and up to about 33 volume percent residual methanol carrier liquid.

Rinse spray gun with distilled water prior to applying Inventors' Titanyl-Oxide Moieties (unless using 2 sprayers, one for each product).

Titanyl-Oxide Moieties Application

Add an aqueous mixture of Inventors' Titanyl-Oxide Moieties to the applicator container.

Fasten the Liquid Hose/Bottle cap assembly tightly on the container.

Connect the air hose from compressor to air fitting on the spray applicator.

Connect the liquid hose to the liquid fitting on the spray applicator.

Plug the power cord into an appropriate receptacle. Turn on the air compressor.

Optimal spraying distance is at least 36 to 48 inches away from the target surface.

Hold the spray gun at right angles to the target surface and spray.

Target surface should just barely glisten with the spray. Do not over-saturate the surface.

Allow target surface to dry, i.e. allow at least 90 weight percent of the water liquid carrier to evaporate to give a deposition consisting essentially of Inventors' Titanyl-Oxide Moieties. The deposition onto the target surface consists of at least 66 volume percent of Inventors' Titanyl-Oxide Moieties and up to about 33 volume percent residual water carrier liquid.

Clean the spray gun with distilled water per manufactures' specifications after each day of use.

TABLES 1-4, set forth in FIGS. 24-27 respectively, recite anti-microbial efficacy data at t=0 and after inoculation of the treated test coupons. Table 2 includes data for ABS-G2020 and ABS-G2030 treated Formica coupons. Table 3 includes data for ABS-G2020 and ABS G-2030 treated stainless steel coupons.

Viral Testing Procedure

1. RAW (mouse macrophage) host cells were prepared in 96-well trays 24 hours prior to use in testing.

2. On the day of testing, a stock vial of test virus, murine norovirus, was removed from storage at −80° C. (titer=5× $10^8$ TCID50 units per ml). An organic soil load (heat-inactivated fetal bovine serum) was added to obtain a final concentration of 5%.

3. Control (non-coated stainless steel and formica) and coated test carriers [ABS-G2015 (SS); ABS-G2020 (Form); ABS-G2030 (Form); ABS-P2015 (SS)] were placed into sterile Petri dishes (one per dish) using pre-sterilized forceps.

4. Viral inocula (0.010 ml) were pipetted onto the center of the control and test carriers, and spread over a surface area of ~1-in$^2$ using a sterile, bent pipette tip.

5. One set of control carriers (per surface material type) was harvested/neutralized immediately to determine Time Zero counts by placement into sterile stomacher bags containing 3 ml of neutralizing solution (calf serum supplemented with 0.001% Na-thiosulfate and 0.001% Na-thioglycollate). The bags were stomached for 120 seconds at high speed to release the viruses from the carriers.

6. The remaining control and test carriers were held under ambient conditions for the duration of each of the specified study contact times of 4 hours and 24 hours [placement distance/configuration: ~68 inches (~1.7 m) below two full-spectrum bulbs, inoculated side facing up towards the lights)]. All carriers were observed to be dried within 10 minutes of inoculation.

7. Upon closure of the respective contact times, the control and test carriers were neutralized by placement into sterile stomacher bags containing 3 ml of neutralizing solution, followed by stomaching as previously described.

8. At the start and finish of each of the contact times, room temperature, relative humidity, and illuminance (lux) were measured and recorded.

9. Control and test carrier eluates were serially diluted (1:10) and plated in replicates of six onto RAW host cells prepared to the appropriate confluency.

10. The plates were observed every 24 to 48 hours to visualize viral cytopathic effects (CPE) and cytotoxicity.

11. Following a 9-day assay incubation period, the plates were formally scored.

12. Log 10 and percent reductions were calculated for each of the test coating formulations relative to the timed control virus counts (per surface type). However, reductions could not be computed for the 24 hour contact time due to insufficient viral recovery from the control carriers.

13. A neutralization validation was performed for each of the test coating formulations (except for ABS-P2015 due to a lack of carriers). One control carrier and one of each test carrier type were placed into stomacher bags containing 3 ml of neutralizer, and processed as previously described. The eluate was serially diluted, and low titer inoculum of the test virus (~3-log 10) was added to each of the dilution tubes per control and test carrier suspension. Aliquots (0.1 ml) of the suspensions were then plated in order to assess cytotoxic levels of the neutralized test materials.

Example VIII

Example VIII compares antimicrobial efficacy of coatings applied by conventional spray technique and coatings applied by electrostatic spray technique. In this example, complete formulations ABS-G2015, AB-G2020, and ABS-G2030 were used, where those coating formulations were disposed on stainless steel test coupons using the full procedure of Example VII. In one set of experiments, the formulations were disposed onto the test coupons using an electrostatic spray assembly. In another set of experiments, the formulations were disposed onto the test coupons using a non-electrostatic spray assembly. The test organism for Example VIII was *E. coli*.

FIGS. 28, 29, and 30 set forth antimicrobial efficacy data for the electrostatic spray embodiments. FIGS. 31, 32, and 33 set forth antimicrobial efficacy data for the non-electrostatic spray embodiments.

Example IX

Example IX demonstrates durability and antimicrobial efficacy of various coatings formed from the electrostatic spray coating of test surfaces with: (1) an aqueous organosilane mixture (with or without an amine present), optionally followed by (2) an aqueous 0.85 wt. % peroxotitanium acid and peroxo-modified anatase sol mixture as disclosed herein.

Internal designations, shorthand codes, are used herein for convenience. Applicants' internal reference coding system includes a silane indicator (2015, 2020, 2030, as explained below), an amine indicator (e.g., "A01" is used to indicate presence of triethanolamine), and the indicator "T," which when present indicates a second coating step using a titanyl sol-gel comprising an 0.85 wt. % aqueous mixture of peroxotitanium acid and peroxo-modified anatase sol as discussed. Thus, for example, the shorthand code of "2015A01T," refers to a sample coupon that was sequentially coated with (1) an aqueous mixture of 3-(trihydroxysilyl)propyl dimethyloctadecyl ammonium chloride (2015) and triethanoamine (A01); followed by (2) a titanyl sol-gel (T). In any experiment that includes "T," the aqueous 0.85 wt. % peroxotitanium acid and peroxo-modified anatase sol mixture was sprayed overtop of an organosilane coating such that the portion of the surface being testing for durability and/or antimicrobial efficacy comprises both coatings, the organosilane and the titanyl species. As mentioned, room temperature drying of the aqueous 0.85 wt. % peroxotitanium acid and peroxo-modified anatase sol mixture may form a crystalline or amorphous $TiO_2$ thin film.

For each of the tests, the antimicrobial coating compositions were as follows (the shorthand internal designations correlate to the experimental results set forth in FIGS. 34-39):

2015: refers to 0.75 wt. % 3-(trihydroxysilyl)propyl dimethyloctadecyl ammonium chloride, remainder water. For each of the 2015 compositions, ProShield® 5000D was the commercial source of the 3-(trihydroxysilyl)propyl dimethyloctadecyl ammonium chloride;

2015A01: refers to 0.75 wt. % 3-(trihydroxysilyl)propyl dimethyloctadecyl ammonium chloride, 0.045 wt. % triethanolamine, remainder water. Triethanolamine was sourced from Sigma-Aldrich;

20152020A01 (5:1:1): refers to 0.75 wt. % 3-(trihydroxysilyl)propyl dimethyloctadecyl ammonium chloride, 0.06 wt. % 3-chloropropyltrimethoxysilane, 0.045 wt. % triethanolamine, remainder water. 3-chloropropyltrimethoxysilane was sourced from Sigma-Aldrich; and 20152020A01 (5:2:1): refers to 0.75 wt. % 3-(trihydroxysilyl)propyl dimethyloctadecyl ammonium chloride, 0.12 wt. % 3-chloropropyltrimethoxysilane, 0.045 wt. % triethanolamine, remainder water.

The single-step coating procedure (organosilane only and no subsequent titanyl species "T") comprised spraying the aqueous organosilane mixture as a fine mist from an electrostatic spray gun at a distance of about 5-6 feet onto the test coupons and allowing the surfaces to dry at room temperature overnight.

The two-step coating procedure (organosilane followed by aqueous 0.85 wt. % peroxotitanium acid and peroxo-modified anatase sol mixture "T") comprised spraying the aqueous organosilane mixture as a fine mist from an electrostatic spray gun at a distance of about 5-6 feet onto the test coupons and allowing the surfaces to visibly dry at ambient conditions for about 3 to 5 minutes. The test coupons were then subsequently coated by aqueous 0.85 wt. % peroxotitanium acid and peroxo-modified anatase sol mixture from an electrostatic sprayer at a distance of 5 to 6 feet and the resulting coated surfaces allowed to dry overnight at room temperature.

This example further includes wear data for the various antimicrobial coatings. Wear data are indicative of the durability of a coating and relate to how well an antimicrobial coating can withstand frequent handling or other insult. An existing EPA Protocol may be used to generate the wear data. In certain instances, the EPA protocol may be modified.

EPA Protocol #01-1A, entitled "Protocol for Residual Self-Sanitizing Activity of Dried Chemical Residues on Hard, Non-Porous Surfaces," is a standard test method used for testing the durability of an antimicrobial coating on a hard surface. The test method utilizes an in-line abrasion machine commonly used in assessing the cleaning ability of detergents. However, instead of a soiled tile being positioned in the machine to be scrubbed, test coupons having an antimicrobial coating are positioned in the machine. The back-and-forth cycling of a weighted scrubber (a weighted "boat" with a cloth or sponge) simulates natural wearing of the antimicrobial coating, such as the wear the surface may experience when frequently handled. In variations of the test protocol, the cloth in the weighted boat may be moist to simulate the handling of surfaces with a moist hand. In various examples, correlations can be made to handling of environmental surfaces, e.g., a doorknob. At various wear cycles, coupons may be weighed for weight loss or inoculated with a test organism.

The abrasion tester suggested in the EPA protocol is a GardCo Washability and Wear Tester, Model D10V, Cat. No. #WA-2153, from the Paul N. Gardner Co., Inc., Pompano Beach, Fla., which is the machine used herein. Variables in the protocol include the weight of the boat, the material wrapped around the boat (e.g., a cloth wiper), the moisture level on the wiper, the speed of the oscillations, and the number of cycles, in addition to the type of coating on the test coupons, the test coupon material, and the arrangement of coated coupons in the machine.

For this Study, the Following Abrasion Protocol was Followed:

Six 2"×2" stainless steel carrier coupons were used, each coupon weighed before and after coating, and before and after abrasion testing.

The wear testing was performed in replicates of two.

TexWipe® cotton wipers (VWR# TWTX309) were used with TexWipe® FoamWipe™ wipers (VWR# TWTX704) as a liner on the weighted boat.

The weight of the boat was adjusted to 1.0 kg with the necessary auxiliary weights.

Using the GardCo Washability machine, a cycle refers to 2 passes of the weighted boat, there and back. Abrasion speed was set to "2.5," which equated to about 4-6 seconds per cycle.

The cotton wiper and foam liner were arranged in the weighted boat. The wiper was sprayed at a distance of 75 cm±1 cm with deionized water for 2 seconds using a Preval Sprayer to moisturize the wiper. Abrasion testing was performed immediately after moisturizing the wiper.

The TexWipe® cotton wiper was replaced after each abrasion cycle.

Test coupons subjected to 10 cycles (10×) or 30 cycles (30×) are then measured for percent weight loss or inoculated with a test organism to measure residual antimicrobial efficacy.

Rinse Testing

In some instances, coated test coupons were subjected to a rinse procedure to test resistance of coatings to wetting without any abrasion. For the rinse testing, coupons were washed three times in 20 mL of deionized water on a shaker at 60 revolutions per minute (rpm) for 10 min.

Biological Testing with *E. coli* 25922:

1. An overnight culture of the test organism, *E. coli* 25922, was initiated by inoculating one colony from a TSA plate into 20 ml of TSB, and incubating under dynamic conditions at 37° C. for 24 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inoculum (0.010 ml) were pipetted onto the center of the control and test carriers, and spread over a surface area of ~1 $in^2$ using a sterile, bent pipette tip.

5. One set of control and test carriers was harvested/neutralized after a 20 min drying period to determine Time Zero counts. The sterilized swabs were dipped in 1 ml D/E broth for 2 seconds and were used to swab the inoculated surface on control and test carriers, followed by vortexing in the rest of D/E Broth to release the bacteria.

6. The remaining control and test carriers were held under ambient conditions for the duration of each of the specified study contact times of 1 hour and 4 hours and all carriers were evaluated in duplicate. The test was performed on two separate occasions, and each time, carriers were evaluated in duplicate.

7. Once the contact times were reached, the control and test carriers were neutralized by swabbing with D/E Broth, followed by vortexing as previously described.

8. Control and test carrier eluates were serially diluted (1:10), and spread-plated onto tryptic soy agar (TSA) plates.

9. The plates were inverted and incubated at 37° C. for 18 to 24 hours, and then scored by directly counting the colonies. Bacterial counts were calculated on a "per carrier" basis. A mean bacterial count was then computed per coating formulation per contact time, as applicable.

10. $Log_{10}$ and percent reductions were calculated for each of the test coating formulations relative to the timed control bacterial counts.

Bacterial Testing with *S. epidermidis* 12228:

1. An overnight culture of the test organism, *S. epidermidis* 12228, was initiated by inoculating one colony from a TSA plate into 20 ml of TSB, and incubating under dynamic conditions at 37° C. for 24 hours prior to testing.

2. On the date of testing, the test culture was removed from incubation, and supplemented with Fetal Bovine Serum (FBS) to achieve a final concentration of 5% (v/v).

3. An overnight density of $10^8$ to $10^9$ colony-forming units (CFU) per ml was assumed. No dilutions of the test organism were performed prior to carrier inoculation. The target inoculum density was $10^6$ to $10^7$ CFU per carrier (or per 0.010 ml).

4. Bacterial inoculum (0.010 ml) were pipetted onto the center of the control and test carriers, and spread over a surface area of ~1 $in^2$ using a sterile, bent pipette tip.

5. One set of control and test carriers was harvested/neutralized after a 20 min drying period to determine Time Zero counts. The sterilized swabs were dipped in 1 ml D/E broth for 2 seconds and were used to swab the inoculated surface on control and test carriers, followed by vortexing in the rest of D/E Broth to release the bacteria.

6. The remaining control and test carriers were held under ambient conditions for the duration of the specified study contact time of 4 hours and all carriers were evaluated in duplicate.

7. Once the contact time was reached, the control and test carriers were neutralized by swabbing with D/E Broth, followed by vortexing as previously described.

8. Control and test carrier eluates were serially diluted (1:10), and spread-plated onto tryptic soy agar (TSA) plates.

9. The plates were inverted and incubated at 37° C. for 18 to 24 hours, and then scored by directly counting the colonies. Bacterial counts were calculated on a "per carrier" basis. A mean bacterial count was then computed per coating formulation per contact time, as applicable.

10. Log$_{10}$ and percent reductions were calculated for each of the test coating formulations relative to the timed control bacterial counts.

Results

In general, the addition of 2020 (3-chloropropyltrimethoxysilane) to an aqueous solution of 2015A01 (3-(trihydroxysilyl)propyl dimethyloctadecyl ammonium chloride and triethanolamine) greatly improved formula storage stability. For example, 20152020A01 (5:2:1) remained entirely transparent for at least 15-days at room temperature. Further, the addition of 3-chloropropyltrimethoxysilane to 2015A01 composition at least somewhat improved durability and antimicrobial efficacy, as explained below.

FIG. 34 sets forth wear data as determined by percent weight loss from coated stainless steel test coupons after 30-cycles of abrasion. As explained, the "T" in each sample ID indicates coupons were spray coated in a two-step process that included the titanyl sol-gel second coating. The tabular data in FIG. 34 show that 3-chloropropyltrimethoxysilane improves the durability of (3-(trihydroxysilyl)propyl dimethyloctadecyl ammonium chloride coatings on a stainless steel surface. In particular, the increase from 61.20% weight percent of coating remaining for the 2015T treated coupons to 76.50% weight percent of coating remaining for the 20152020A01T (5:2:1) treated coupons demonstrates the unexpected effect of 3-chloropropyltrimethoxysilane.

FIG. 35 sets forth percent weight loss data obtained for stainless steel coupons previously coated with 2015T, 2015A01T, 20152010A01T (5:1:1) or 20152020A01T (5:2:1) and then subjected to the rinse protocol described or 10-cycles of abrasion in the washability machine. The individual studies PR59 through PR90 are averaged in the last row of the table of FIG. 35, recognizing that some averages included many more replicate studies than other averages in the table. In the rinsing test portion of the averaged data, 2015T, 2015A01T and 20152020A01T (5:2:1) showed 47.01%, 48.86% and 56.36% of the weight of the coating remaining, respectively, after the rinsing protocol, (see averaged data in FIG. 35). These results demonstrate an improvement in the water resistance of a 3-(trihydroxysilyl)propyl dimethyloctadecyl ammonium chloride and triethanolamine coating by having 3-chloropropyltrimethoxysilane in the coating composition.

Figure 36:
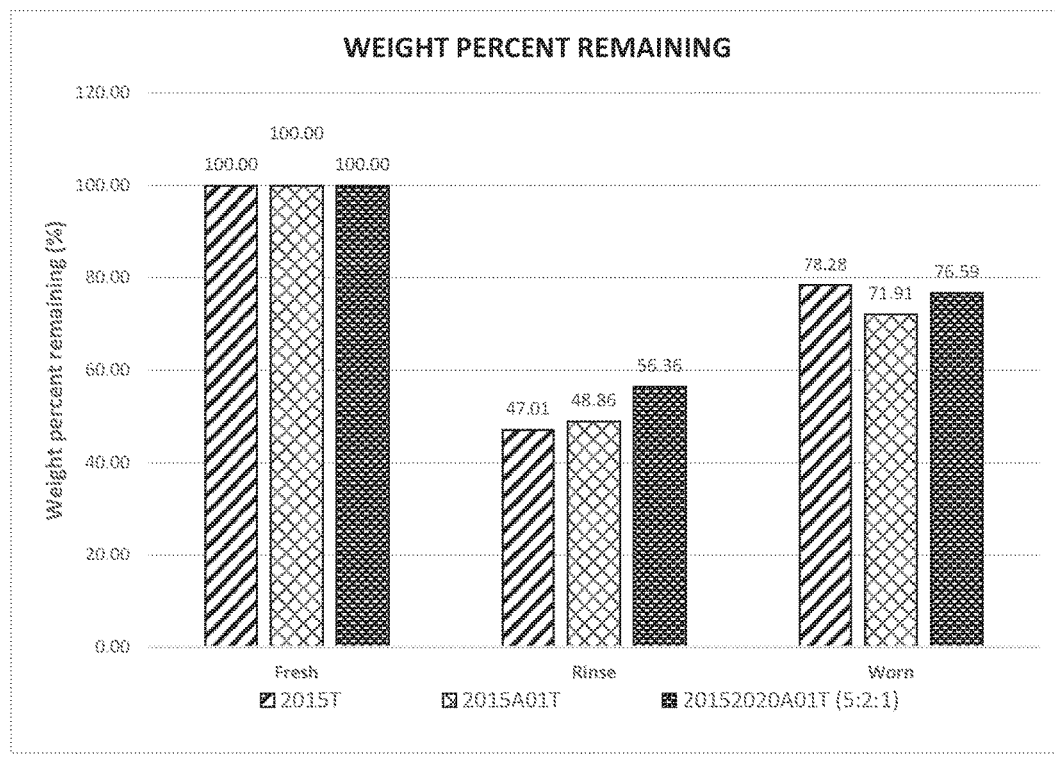
FIG. 36 sets forth averaged weight loss data for various coatings subjected to rinsing or subjected to 10-cycles of abrasion in an in-line washability machine, in both tabular and bar chart formats, in accordance with various embodiments.

FIG. 36 shows averaged weight percent remaining after coated coupons were subjected to either the rinsing protocol or 10-cycles of abrasion in the washability machine. From the data of FIG. 36, it is evident that the presence of 3-chloropropyltrimethoxysilane improves the water resistance of a coating comprising (3-(trihydroxysilyl)propyl dimethyloctadecyl ammonium chloride, (e.g., 56.36% weight remaining for 20152020A01T (5:2:1) coated coupons versus only 48.86% weight remaining for 2015A01T coated coupons). Further, it is evidence that the presence of 3-chloropropyltrimethoxysilane improves the abrasion resistance of a coating comprising (3-(trihydroxysilyl)propyl dimethyloctadecyl ammonium chloride, (e.g., 76.59% weight remaining for 20152020A01T (5:2:1) coated coupons versus only 71.91% weight remaining for 2015A01T coated coupons).

FIG. 37 sets forth the residual antimicrobial efficacy of 2015T, 2015A01T, 20152020A01T (5:1:1) and 20152020A01T (5:2:1) for coatings on stainless steel subjected to the rinse protocol or 10-cycles in the washability machine. The table in FIG. 37 also sets forth averaged data in the last row of the table, recognizing that the number of replicate tests is not necessarily the same for each of the averages. Antimicrobial efficacy was determined for freshly coated coupons, coupons subjected to the water rinsing protocol, and coupons subjected to 10-cycles on the washability machine, against *E. coli* 25922 at 4-hours contact time for the inoculum on the coupon. The data show a somewhat sustainable efficacy against *E. coli* 25922 by including 3-chloropropyltrimethoxysilane in the 3-(trihydroxysilyl)propyl dimethyloctadecyl ammonium chloride and triethanolamine coatings, most notably shown by the maintenance of a 0.81 log kill efficacy by the 20152020A01T (5:2:1) coating on stainless steel subjected to 10-cycles of abrasion compared to 0.58 log kill for similarly abraded 2015A01T coated coupons. For rinsed coupons, the benefits of 3-chloropropyltrimethoxysilane are not seen when assessing water resistance by antimicrobial efficacy.

As shown in FIG. 38, some maintenance of the efficacy against *S. epidermidis* 12228 from the addition of 3-chloropropyltrimethoxysilane to the 3-(trihydroxysilyl)propyl dimethyloctadecyl ammonium chloride and triethanolamine composition was observed for rinsed coupons and coupons subjected to 10-cycles of abrasion. After subjecting coated coupons to the rinsing protocol, 2015A01T coated coupons showed only 0.07 log kill against *S. epidermidis* 12228 after 4-hours contact time, whereas 20152020A01T (5:2:1) coated coupons retained a 0.21 log kill against *S. epidermidis* 12228 after 4-hours contact time. For the 10-cycle abraded coupons, 2015A01T treated coupons retained only 0.08 log kill, whereas the 20152020A01T (5:2:1) treated coupons still retained a 0.32 log kill against *S. epidermidis* 12228 after 4-hours contact time. The retention of greater antimicrobial efficacy correlate to the retention of more coating on a stainless steel coupon after rinsing or after mechanical abrasion when the coating also comprises 3-chloropropyltrimethoxysilane.

Figure 39:
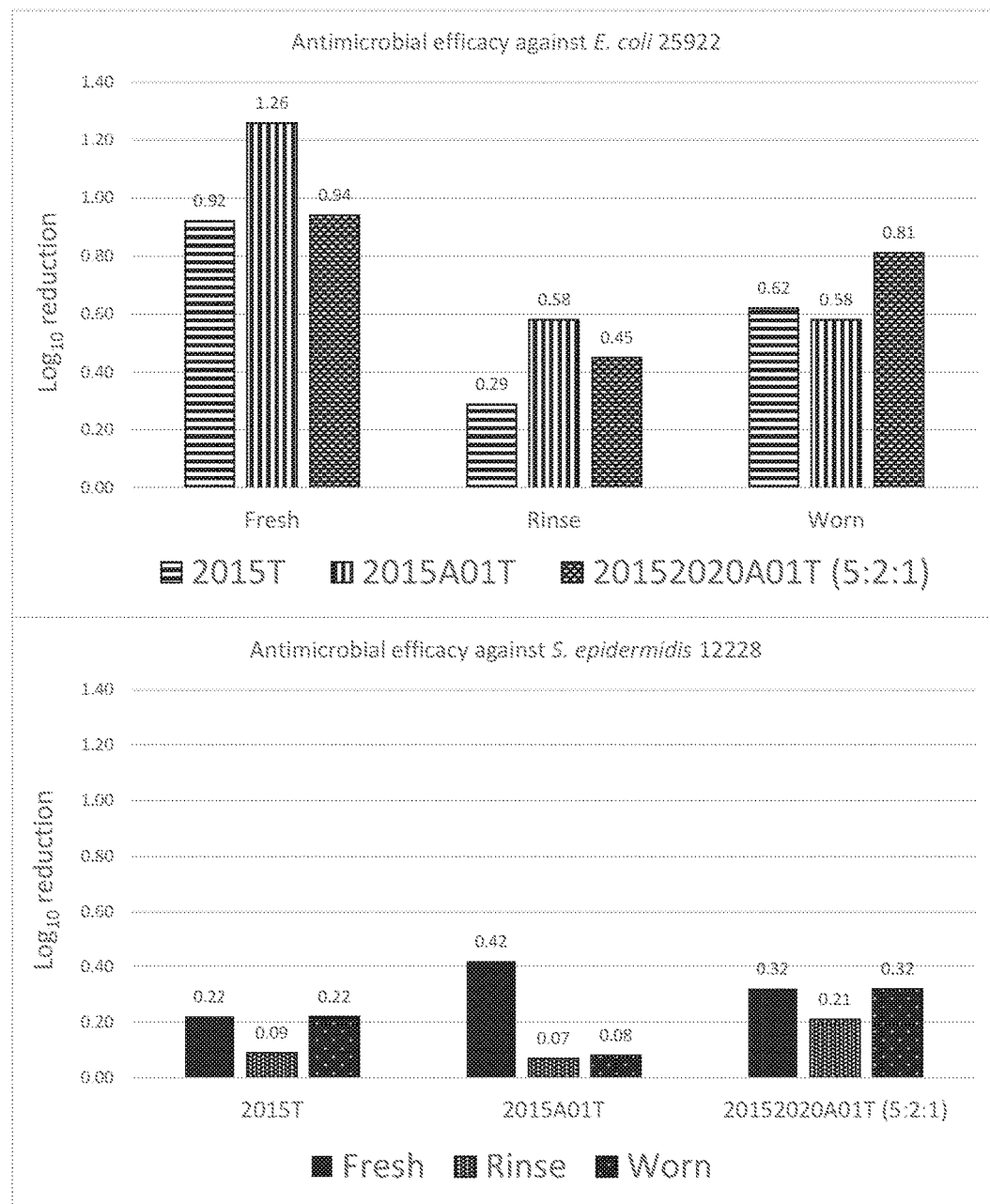
FIG. 39 graphically displays the averaged data set forth in FIG. 37 (*E. coli* 25922) and FIG. 38 (*S. epidermidis* 12228) as bar graphs.

The bar charts in FIG. 39 present the same residual antimicrobial efficacy data in graphical form for clarity. The results of EXAMPLE IX show an unexpected benefit when including 3-chloropropyltrimethoxysilane in a coating comprising 3-(trihydroxysilyl)propyl dimethyloctadecyl ammonium chloride and triethanolamine, overcoated with titanyl sol-gel.

Example X

Stainless steel carriers were coated with the solutions containing 7.5% of one of three different choline 16 compounds in H$_2$O, wherein R3 is selected from the group consisting of —H and —CO—CH$_3$. Cholines used included Choline Chloride, Choline Bitartrate, and Acetylcholine Chloride. Carriers were coated by dipping into solution using forceps and allowing to drip-dry overnight. Carriers were still not completely dry even after 24 hours drying time. Twenty (20) microliters of O/N cultures of *E. coli* 25592 (grown at 37 C for 18 hours) were added to each carrier. Following inoculation of the carriers, the carriers were swabbed with D/E neutralizing broth and processed for the zero hour time point. This was repeated for the 1 and 4 hour time points.

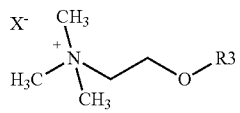

16

The collected samples were then diluted in PBS and 100 microliters were plated on to TSA plates and left overnight at 37° C. before counting and calculating CFU/ml. All carriers were tested in duplicate and two experiments were performed (A and B in data tables) in tandem. All data is represented as the mean+/−the SEM (standard error) when applicable.

When calculated relative to the timed control, choline bitartrate showed the greatest surface-kill, with a 2.39 log reduction in bacteria. Acetylcholine chloride and choline chloride showed a 1.85 and 1.40 log reduction, respectively. When compared with the results of aqueous solutions of Aminopropyl triethoxysilane (APTES) and the cholines at the same concentration, it is clear that these solutions are much more antimicrobial than the cholines on their own. APTES+Choline Chloride and APTES+Choline Bitartrate showed a 3.36 and 3.38 log reduction, respectively, at the 1 hour time point.

TABLE 24 in FIG. 40 recites antimicrobial efficacy data for the above-described choline formulations at time $T_0$, i.e. immediately after inoculation. TABLE 25 in FIG. 41 recites antimicrobial data at one (1) hour after inoculation.

Stainless steel carriers were coated with solutions containing 7.5% of each choline compound and 5% Aminopropyltriethoxysilane in $H_2O$ (ABS-2040 contains choline chloride, while ABS-2041 contains choline bitartrate). Carriers were coated using an electrostatic sprayer and then allowed to dry. Carriers were still not completely dry even after 2 days of drying time. Twenty (20) microliters cultures of *E. coli* grown at 37° C. for 18 hours) were added to each carrier. Following inoculation of the carriers, the carriers were swabbed with neutralizing broth and processed for the zero hour time point. This was repeated for the 1 hour time point.

The collected samples were then diluted in PBS and 100 microliters were plated on to TSA plates and left 0/N at 37 C before counting and calculating CFU/ml. All carriers were tested in duplicate and two experiments were performed (A and B in data table) in tandem. All data is represented as the mean+/−the SEM (standard error) when applicable. It is worth noting that colonies on the Choline Bitartrate plates were significantly smaller than the others.

TABLE 26 in FIG. 42 recites antimicrobial efficacy data at time $T_0$, i.e. immediately after inoculation. TABLE 27 in FIG. 43 recites antimicrobial data at one (1) hour after inoculation. TABLE 28 in FIG. 44 recites antimicrobial data at four (4) hours after inoculation.

Stainless steel carriers were coated with solutions containing 15% of each choline compound and 5% Aminopropyltriethoxysilane in $H_2O$ (ABS-2040 contains choline chloride, while ABS-2041 contains choline bitartrate). Carriers were coated using an electrostatic sprayer and then allowed to dry. Carriers were still not completely dry even after 2 days of drying time. 20 microliters of cultures of *E. coli* 25592 grown at 37° C. for 18 hours were added to each carrier. Following inoculation of the carriers, the carriers were swabbed with D/E neutralizing broth and processed for the zero hour time point. This was repeated for the 1 and 4 hour time points.

The collected samples were then diluted in PBS and 100 microliters were plated on to TSA plates and left 0/N at 37° C. before counting and calculating CFU/ml. All carriers were tested in duplicate and two experiments were performed (A and B in data table) in tandem. All data is represented as the mean+/−the SEM (standard error) when applicable.

TABLE 29 in FIG. 45 recites antimicrobial efficacy data at time $T_0$, i.e. immediately after inoculation. TABLE 30 in FIG. 46 recites antimicrobial data at one (1) hour after inoculation. TABLE 31 in FIG. 47 recites antimicrobial data at four (4) hours after inoculation.

In coating formulations ABS 2015E, 2020E, and 2030E, depending on the stoichiometry of the mixture of triethanolamine and the organosilane, one or polymeric species are formed on a treated surface.

In various embodiments, and as shown in Reaction Scheme 2, triethanolanmine 9 and organosilane 1 can react to form a linear polymer 10, wherein n is greater than or equal to 1 and less than or equal to 10.

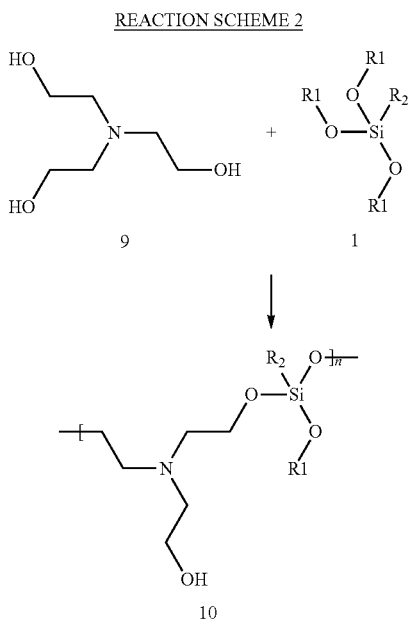

REACTION SCHEME 2

In other embodiments, and as shown in Reaction Scheme 3, triethanolamine 9 and organosilane 1 react to form a branched polymer 11.

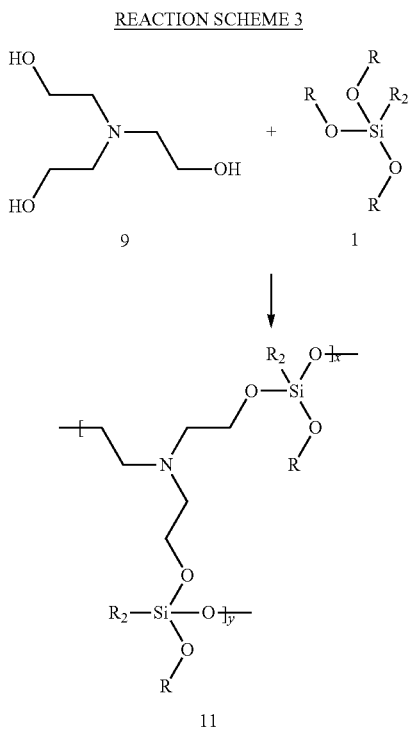

REACTION SCHEME 3

Wherein in Reaction Scheme 3, x is greater than or equal to 1 and less than or equal to about 10, and wherein y is greater than or equal to 1 and less than or equal to about 10.

In other embodiments, and as shown in Reaction Scheme 4, triethanolamine 9 and organosilane 1 react to form a cross-linked polymer 12.

REACTION SCHEME 4

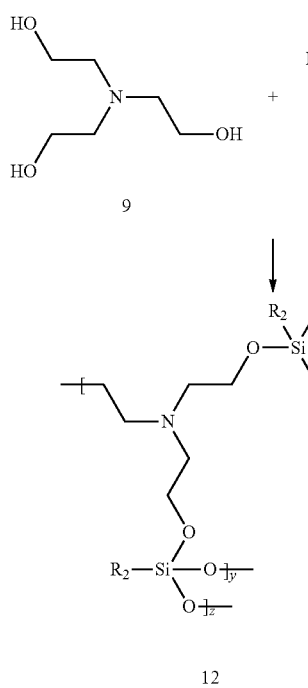

12

Wherein in Reaction Scheme 4, x is greater than or equal to 1 and less than or equal to about 10, and wherein y is greater than or equal to 1 and less than or equal to about 10, and wherein z is greater than or equal to 1 and less than or equal to about 10.

In various embodiments, Inventors' organosilane comprises tetraethylorthosilicate 13. In various embodiments and as shown in Reaction Scheme 5 and depending on the stoichiometry of the starting materials 9 and 13, Inventors' cross-linked polymeric material 14 is formed by reaction of tetraethylorthosilicate 13 and triethanolamine 9. Reaction Scheme 5 illustrates a single Si atom having four (4) different polymer chains originating therefrom. Those skilled in the art will appreciate that Inventors' cross-linked polymer material 14 comprises a very high cross-link density.

REACTION SCHEME 5

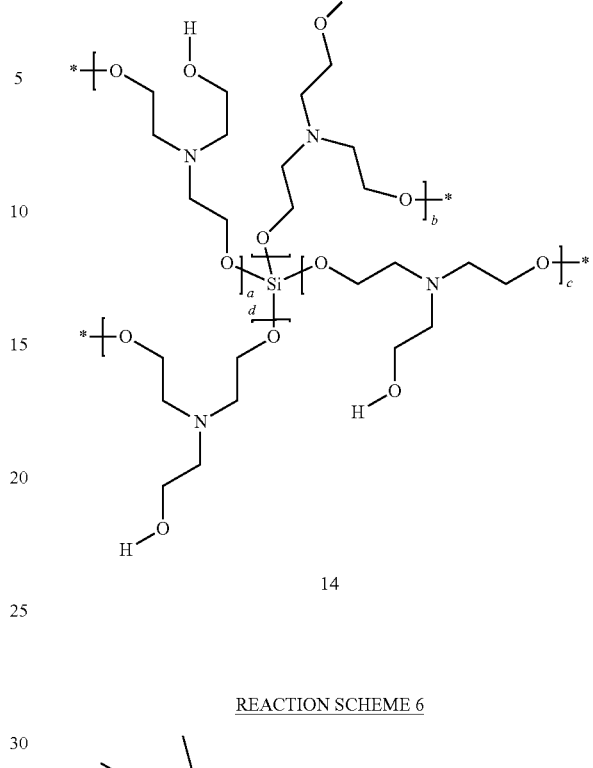

14

REACTION SCHEME 6

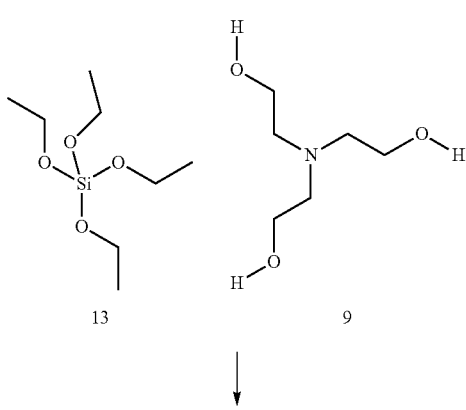

15

Wherein in Reaction Scheme 6, a is greater than or equal to 1 and less than or equal to about 10, and wherein b is greater than or equal to 1 and less than or equal to about 10, and wherein c is greater than or equal to 1 and less than or equal to about 10, and wherein d is greater than or equal to 1 and less than or equal to about 10.

Sterilization Station Example

Figure 3:
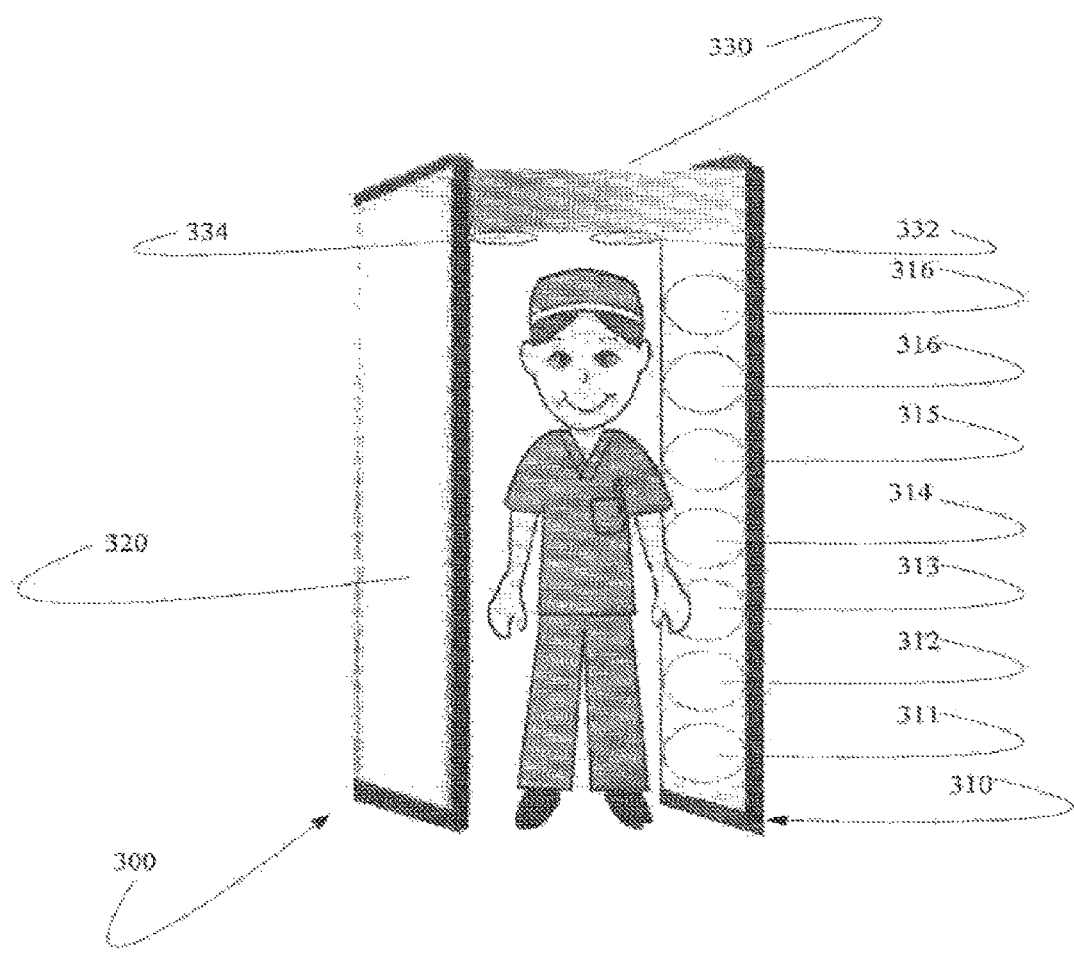
FIG. 3 illustrates Applicants' sterilizing station 300, in accordance with various embodiments.

Referring now to FIG. 3, Applicants' sterilizing station 300 comprises a "walk through" assembly having two opposing sides 310 and 320 which are joined by top 330. In the illustrated embodiment of FIG. 3, side 310 comprises a plurality of UV light emitters 311, 312, 313, 314, 315, 316, and 317, where that plurality of UV emitters face the interior, i.e. walking space portion, of sterilizing station 300. In other embodiments, Applicants' sterilizing station 300 comprises fewer than seven (7) UV emitters per side. In various embodiments, Applicants' sterilizing station comprises more than seven (7) UV emitters per side.

Side 320 is similarly formed to include a plurality of UV emitters, where each of those UV emitters face the interior, i.e. walking space portion, of sterilizing station 300. The plurality of UV emitters disposed on the interior portion of side 310 have a facing relationship with the plurality of UV emitters disposed on the interior portion of side 320.

Further in the illustrated embodiment of FIG. 3, top portion 330 comprises a plurality of UV emitters, i.e. UV emitters 332 and 334, where those UV emitters face downwardly. In other embodiments, top portion 330 comprises more than two (2) UV emitters.

The illustrated embodiment of FIG. 3 shows a medical practitioner walking through sterilizing station 300. The medical practitioner is wearing a scrub suit, the various pieces of which have been coated on the exterior surface with Applicants' coating composition. As the practitioner walks through sterilizing station 300, the plurality of UV emitters disposed on sides 310 and 320, and the plurality of UV emitters disposed on top 330, are energized thereby maximizing the photocatalytic effect of Applicants' coating. Enhancing the photocatalytic activity of the coating maximizes the production of high energy, atomic oxygen species at the surface of scrub suit pieces, thereby, effectively sterilizing the exterior surfaces of all scrub suit articles.

While the various embodiments of the present disclosure have been illustrated in detail, it should be apparent that modifications and adaptations to those embodiments may occur to one skilled in the art without departing from the scope of the present disclosure as set forth herein.

Antimicrobial coating compositions, methods of applying antimicrobial coating compositions and antimicrobial coatings on surfaces are provided. When a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in various embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or system or any components thereof or methods of making and using same to address each and every problem sought to be solved by the present disclosure, for it to be encompassed by the present claims.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. A method of preparing an antimicrobial coating on a portion of a surface, the method comprising:
    disposing an aqueous antimicrobial coating composition comprising from about 0.5 wt. % to about 1.0 wt. % 3-(trihydroxysilyl)propyl dimethyloctadecyl ammonium chloride and from about 0.01 wt. % to about 0.10 wt. % triethanolamine, remainder water, on the portion of the surface; and
    disposing an aqueous titanyl sol-gel on the portion of the surface overtop of the aqueous antimicrobial coating composition,
    wherein the antimicrobial coating thus formed exhibits residual antimicrobial efficacy against *E. coli* and *S. epidermidis* after exposure to water rinsing or mechanical abrasion.

2. The method of claim 1, wherein the titanyl sol-gel comprises 0.85 wt. % peroxotitanium acid and peroxo-modified anatase sol mixture, with the remainder of the sol-gel being water.

3. The method of claim 1, wherein the aqueous antimicrobial coating composition further comprises 3-chloropropyltrimethoxysilane.

4. The method of claim 3, wherein the aqueous antimicrobial coating composition comprises about 0.75 wt. % 3-(trihydroxysilyl)propyl dimethyloctadecyl ammonium chloride, about 0.06 wt. % 3-chloropropyltrimethoxysilane, and about 0.045 wt. % triethanolamine, with the remainder of the aqueous antimicrobial coating composition being water.

5. The method of claim 4, wherein the resulting antimicrobial coating retains about 63% of its weight after 10-cycles of abrasion in a straight-line washability machine equipped with a 1 kg weighted boat wrapped in a water-moisturized wiper.

6. The method of claim 4, wherein the resulting antimicrobial coating retains about 67% of its weight after 30-cycles of abrasion in a straight-line washability machine equipped with a 1 kg weighted boat wrapped in a water-moisturized wiper.

7. The method of claim 3, wherein the aqueous antimicrobial coating composition comprises about 0.75 wt. % 3-(trihydroxysilyl)propyl dimethyloctadecyl ammonium chloride, about 0.12 wt. % 3-chloropropyltrimethoxysilane, and about 0.045 wt. % triethanolamine, with the remainder of the aqueous antimicrobial coating composition being water.

8. The method of claim 7, wherein the resulting antimicrobial coating retains about 77% of its weight after 10-cycles of abrasion in a straight-line washability machine equipped with a 1 kg weighted boat wrapped in a water-moisturized wiper.

9. The method of claim 7, wherein the resulting antimicrobial coating retains about 76.5% of its weight after 30-cycles of abrasion in a straight-line washability machine equipped with a 1 kg weighted boat wrapped in a water-moisturized wiper.

10. A method of preparing an antimicrobial coating on a portion of a surface, the method comprising:
   spray coating an aqueous antimicrobial coating composition comprising about 0.75 wt. % 3-(trihydroxysilyl)propyl dimethyloctadecyl ammonium chloride, about 0.06 wt. % 3-chloropropyltrimethoxysilane, and about 0.045 wt. % triethanolamine, remainder water, on the portion of the surface;
   allowing the aqueous antimicrobial coating composition to visibly dry on the portion of the surface;
   disposing an aqueous titanyl sol-gel comprising about 0.85 wt. % of a mixture of peroxotitanium acid and peroxo-modified anatase sol in water on the portion of the surface overtop of the dried aqueous antimicrobial coating composition; and
   allowing the aqueous sol-gel to dry to provide the antimicrobial coating.

11. The method of claim 10, wherein the resulting antimicrobial coating exhibits residual antimicrobial efficacy against *E. coli* and *S. epidermidis* after water rinsing or after mechanical abrasion.

12. The method of claim 10, wherein the resulting antimicrobial coating retains about 48% of its weight after exposure to water rinsing.

13. The method of claim 10 wherein the resulting antimicrobial coating retains about 63% of its weight after exposure to 10-cycles of abrasion in a straight-line washability machine equipped with a 1 kg weighted boat wrapped in a water-moisturized wiper.

14. The method of claim 10, wherein the resulting antimicrobial coating retains about 67% of its weight after 30-cycles of abrasion in a straight-line washability machine equipped with a 1 kg weighted boat wrapped in a water-moisturized wiper.

15. A method of preparing an antimicrobial coating on a portion of a surface, the method comprising:
   spray coating an aqueous antimicrobial coating composition comprising about 0.75 wt. % 3-(trihydroxysilyl)propyl dimethyloctadecyl ammonium chloride, about 0.12 wt. % 3-chloropropyltrimethoxysilane, and about 0.045 wt. % triethanolamine, remainder water, on the portion of the surface;
   allowing the aqueous antimicrobial coating composition to visibly dry on the portion of the surface;
   disposing an aqueous titanyl sol-gel comprising about 0.85 wt. % of a mixture of peroxotitanium acid and peroxo-modified anatase sol in water on the portion of the surface overtop of the dried aqueous antimicrobial coating composition; and
   allowing the aqueous sol-gel to dry to provide the antimicrobial coating.

16. The method of claim 15, wherein the resulting antimicrobial coating exhibits residual antimicrobial efficacy against *E. coli* and *S. epidermidis* after water rinsing or after mechanical abrasion.

17. The method of claim 15, wherein the resulting antimicrobial coating retains about 56% of its weight after exposure to water rinsing.

18. The method of claim 15, wherein the resulting antimicrobial coating retains about 77% of its weight after exposure to 10-cycles of abrasion in a straight-line washability machine equipped with a 1 kg weighted boat wrapped in a water-moisturized wiper.

19. The method of claim 15, wherein the resulting antimicrobial coating retains about 76.5% of its weight after exposure to 30-cycles of abrasion in a straight-line washability machine equipped with a 1 kg weighted boat wrapped in a water-moisturized wiper.

20. A method of preparing an antimicrobial coating on a portion of a surface, the method comprising:
   disposing an aqueous antimicrobial coating composition comprising 3-(trihydroxysilyl)propyl dimethyloctadecyl ammonium chloride and triethanolamine on the portion of the surface; and
   disposing an aqueous titanyl sol-gel on the portion of the surface overtop of the aqueous antimicrobial coating composition, the aqueous titanyl sol-gel comprising 0.85 wt. % peroxotitanium acid and peroxo-modified anatase sol mixture, with the remainder of the sol-gel being water,
   wherein the antimicrobial coating thus formed exhibits residual antimicrobial efficacy against *E. coli* and *S. epidermidis* after exposure to water rinsing or mechanical abrasion.

* * * * *